United States Patent [19]

Sakata

[11] Patent Number: 5,496,734
[45] Date of Patent: Mar. 5, 1996

[54] TREATMENT METHOD FOR BLOOD ANALYSIS

[75] Inventor: Takashi Sakata, Kakogawa, Japan

[73] Assignee: TOA Medical Electronics Co., Ltd., Japan

[21] Appl. No.: 458,304

[22] Filed: Jun. 2, 1995

Related U.S. Application Data

[63] Continuation of Ser. No. 154,795, Nov. 19, 1993, abandoned.

[30] Foreign Application Priority Data

Nov. 19, 1992 [JP] Japan .................................. 4-310146

[51] Int. Cl.$^6$ .................................................. G01N 33/48
[52] U.S. Cl. ............................ 436/63; 436/10; 436/17; 436/172; 436/175; 436/176; 436/800; 435/2
[58] Field of Search ................................ 436/8, 16, 17, 436/10, 63, 172, 174, 175, 176, 800, 56; 435/2, 4, 29, 30, 34, 39, 240.2

[56] References Cited

U.S. PATENT DOCUMENTS

| | | | |
|---|---|---|---|
| 4,286,963 | 9/1981 | Ledis et al. | 436/63 |
| 4,485,175 | 11/1984 | Ledis et al. | 436/10 X |
| 4,528,274 | 7/1985 | Carter et al. | 436/18 X |
| 4,745,071 | 5/1988 | Lapicola et al. | 436/17 X |
| 4,751,188 | 6/1988 | Valet | 436/10 X |
| 4,933,293 | 6/1990 | Kuroda et al. | 436/63 |
| 4,962,038 | 10/1990 | Carter et al. | 436/17 X |
| 5,039,613 | 8/1991 | Matsuda et al. | 436/17 |
| 5,175,109 | 12/1992 | Sakata et al. | 436/17 |
| 5,232,857 | 8/1993 | LeFevre et al. | 436/10 |
| 5,242,832 | 9/1993 | Sakata | 436/10 X |
| 5,250,437 | 10/1993 | Toda et al. | 436/10 |
| 5,256,571 | 10/1993 | Hurley et al. | 436/17 |
| 5,262,329 | 11/1993 | Carver, Jr. | 436/17 X |
| 5,264,369 | 11/1993 | Sakata et al. | 436/63 |
| 5,296,378 | 3/1994 | Sakata et al. | 436/63 |
| 5,308,772 | 5/1994 | Sakata et al. | 436/63 |
| 5,389,549 | 2/1995 | Hamaguchi et al. | 436/10 |
| 5,434,081 | 7/1995 | Maekawa | 436/17 |

FOREIGN PATENT DOCUMENTS

| | | |
|---|---|---|
| 0177137 | 7/1985 | European Pat. Off. . |
| 0259834 | 3/1988 | European Pat. Off. . |
| 0398652 | 5/1990 | European Pat. Off. . |
| 0430750A1 | 6/1991 | European Pat. Off. . |
| 0444241A1 | 9/1991 | European Pat. Off. . |
| 0485945A3 | 5/1992 | European Pat. Off. . |
| 0562877A3 | 9/1993 | European Pat. Off. . |

OTHER PUBLICATIONS

Int'l. Publication No. WO 91/17436—Nov. 14, 1991.
WPI Database, Week 9011, Derwent Publications Ltd., abstract of JP 2031162 A.
Int'l. Publication No. WO84/03771—Sep. 27, 1984.
Int'l. Publication No. WO84/02777—Jul. 19, 1984.

Primary Examiner—James C. Housel
Assistant Examiner—Maureen M. Wallenhorst

[57] ABSTRACT

The present invention is a method for blood analysis which provides a rapid treatment of a blood sample so that it can be analysed for counting and classification of leukocytes. Leukocytes are permeablized by treatment with a surfactant solution and labeled, preferably with a fluorescent dye. The method provides labeled leukocytes that can be counted and classified by optical means, including flow cytometry by analysis of a fluorescence signal.

14 Claims, 24 Drawing Sheets

5,496,734

TREATMENT METHOD FOR BLOOD ANALYSIS

This application is a continuation of application Ser. No. 08/154,795 filed on Nov. 19, 1993, now abandoned.

BACKGROUND OF THE INVENTION

1. Field of the Invention

The present invention relates to a method for classifying and counting a specific cell in the field of clinical testing or cell study. More particularly, it relates to a method for labeling leukocytes contained in a blood sample.

2. Related Art

Generally, in a case of determining a specific cell contained in a biological sample such as blood and urine, containing a variety cells, if the appearance of the cells (such as size and shape) is significantly different among them, it is not difficult to distinguish one from others by using a conventional microscope of transmitted light type. For example, since erythrocytes, leukocytes and blood platelets contained in blood are different in size and shape from each other, they can be easily distinguished.

In contrast, it is difficult to classify cells having a similar appearance with each other. For example, lymphocytes, monocytes, neutrophils, eosinophils and basophils; which belong to subclasses of leukocytes; are not easily classified. In general laboratories, components contained in cells such as a nucleus, granules, cytoplasm and endoenzyme in a leukocyte are stained with an appropriate dyeing solution to visualize the existence of the components contained in the cell and their amount and localization, thereby classifying the cells and providing for their counting.

In other case, a device for measuring cell volume or a device for measuring a scattered light or fluorescence polarized light from a cell is utilized instead of using a microscope. Cells are detected by such a device by measuring the distinctive signals depending on the characteristics of the respective cell in order to classify the cells. If the distinctive signals are not obtained only by using such device, the cells are subjected to a suitable treatment so as to obtain available signals which are different among the cells. Examples of such treatments include a method for lysing cells other than a specific objective cell with a suitable cell lysing agent or a method for detecting the difference in volume of cells, or optical difference of scattered light, fluorescent light, absorbency, or the like. In order to detect the optical difference by using a scattered light, fluorescent light, absorbency and the like, it is preferred to combine a suitable labeling substance such as a dye with at least one component in the cell.

It is known that components contained in cells are separated from the outside by a membrane, called a cell membrane, such that the components do not leak from the cell. However, the cell membrane does not work for complete sealing from the outside. Rather, some substances necessary for survival of the cell are incorporated into the cell and waste products unnecessary for the cell are excreted from the cell. Thus, the cell membrane selects substances accurately and ingeniously to allow substances to pass through. Substances inside and outside the cell pass through various channels for ion passage provided in the membrane and pass through a lipid bilayer by dispersion. Such selective movement of substances continues so long as the cell is alive, but when the cell dies, the selective operation is lost. In accordance with this phenomena, a method for distinguishing live cells from dead cells is known as a dye-exclusion test, in which a dye which can invade into a damaged cell but can not invade into an undamaged cell is used as a labeling substance. An example of the well-known dye-exclusion test is to use a dye such as trypan blue and eosin.

However, such a known method is not always carried out easily. That is, it is not possible to incorporate a labeling substance such as a dye into cells because cells naturally refuse the invasion of unnecessary substances to themselves, or even if it is possible it takes a long time. Generally, when cells are stained, various fixations are performed on the cells to inhibit the invasion function or prevent deformation of the cell and leak of components contained in the cell. In general, aldehydes such as formalin and glutaraldehyde, or methanol and acetone are used as a fixing agent. However, the use of such these fixing agents suffers from drawbacks such as involving a risk in handling and necessity for detoxifying waste water because of their toxicity, which is not a low, or requiring a long time, and a troublesome process for fixation.

On the other hand, a method for generating optical difference without fixing is also known, in which the selective substance exclusion function of the cell membrane is inhibited to assist in combing the cell components with a dye which generally can not pass through the cell membrane. A well known example comprises the steps of lysing the cell membrane and cytoplasm with a nonionic surfactant such as Triton X-100; staining the remaining nuclei with propidium iodide, ethidium bromide, etc. to prepare a test sample; followed by measuring a fluorescence light of the cell by a flow cytometer, microspectrophotometer, etc. and determining an amount of DNA. However, Triton X-100 lyses cell membranes and cytoplasms, and it also damage nuclei to no small extent, so that the data of DNA amount is made inaccurate. Accordingly, stabilization of nuclei, for example adding a stabilizer such as spermidine [N-(3-aminopropyl-1,4-butanediamine] or conducting some other fixation is necessitated in this method. Moreover, as the nuclei are naked, it is not possible to precisely classify leukocytes into each subclass by using scattered light and the like.

It is known to use two kinds of quaternary ammonium salt type surfactants for classifying leukocytes into two types i.e., mononucleocyte group and granulocyte group and analyzing them (for example disclosed in WO84/03771 and WO84/02777). However, the concentration of the surfactants is high, for example, 40 to 70 g/l for one quaternary ammonium salt type surfactant and 2 to 7 g/l for another, which destroys leukocytes themselves and results in naked nuclei, so that it was not possible to classify and counting leukocytes by measuring optical difference.

Japanese Laid-Open Patent Application 88896/1986 discloses a method and a reagent for classifying and counting basophils which belong to leukocytes by using a water soluble surfactant in the limited pH range of 1.8 to 2.3 with a blood sample to generate an optical difference of the basophils. However, the surfactant is also used at a high concentration of 10 to 20 g/l and the method fails to disclose the use of a labeling substance.

SUMMARY OF THE INVENTION

The present invention provides a pretreatment method for blood analysis which comprises selective labeling of leukocytes by treating a blood sample with an aqueous solution comprising at least one surfactant selected from the group consisting of a cationic surfactant and an amphoteric surfactant, and with a labeling substance in which; the aqueous solution of the surfactant is used at a concentration that does not destroy the whole cell membrane of a leukocyte but is sufficient to slightly damage a part of the cell membrane so as to make it permeable. The labeling substance is any substance which is capable of passing through the damaged cell membrane and combining with a component contained in the treated leukocyte; and the treatment is performed at a pH of 3.0 to 11.0.

According to the method of the present invention, only leukocytes can be selectively labeled in a simple manner by using an untreated blood sample, and classified and counted by an optical means.

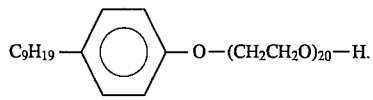

Figure 16:
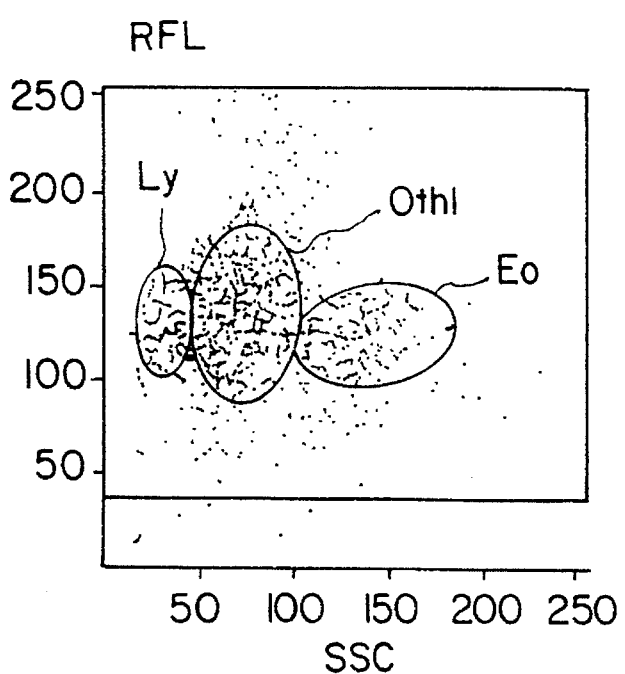

FIG. 16 is a scattergram showing the relationship between the intensity of the side scattered light (SSC) and the intensity of the red fluorescence light (RFL) when a blood sample is treated with a nonionic surfactant having the following formula:

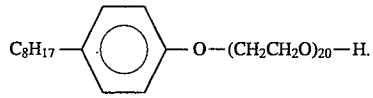

Figure 17:
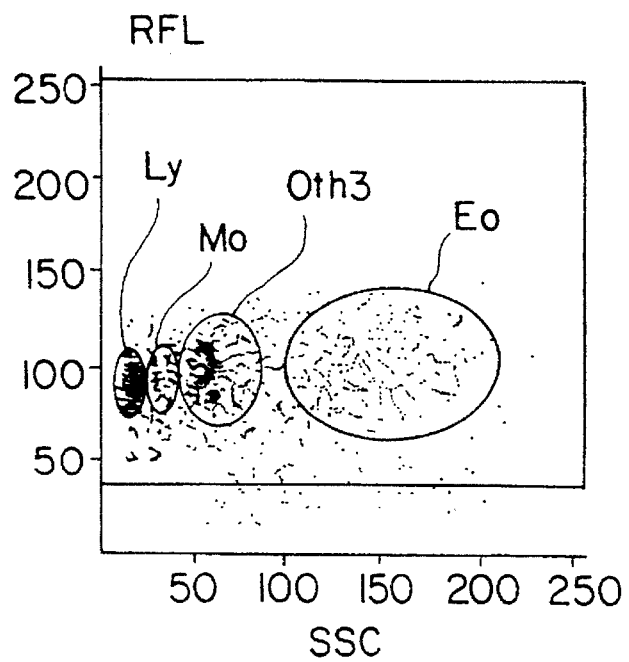

FIG. 17 is a scattergram showing the relationship between the intensity of the side scattered light (SSC) and the intensity of the red fluorescence light (RFL) when a blood sample is treated with a cationic surfactant by adding ethanol (100 ml/l) as an aqueous alcohol.

Figure 18:
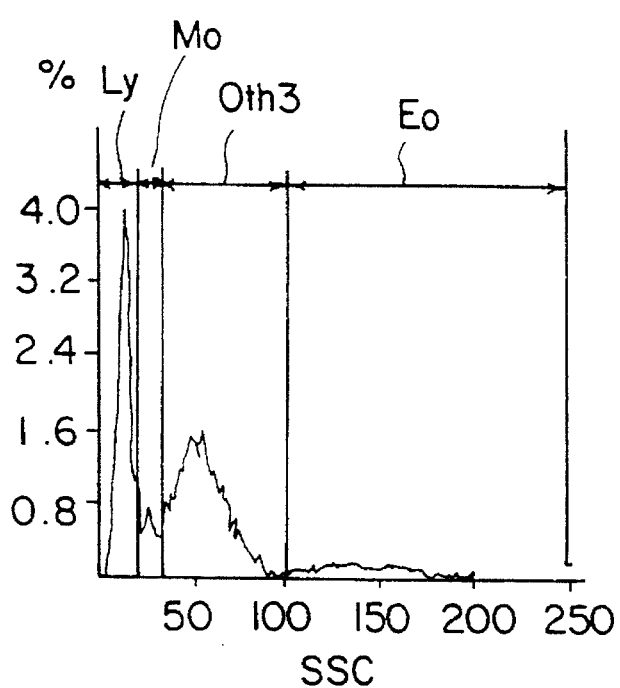

FIG. 18 is a histogram of the side scattered light when a blood sample is treated with a cationic surfactant by adding ethanol (100 ml/l) as an aqueous alcohol.

Figure 19:
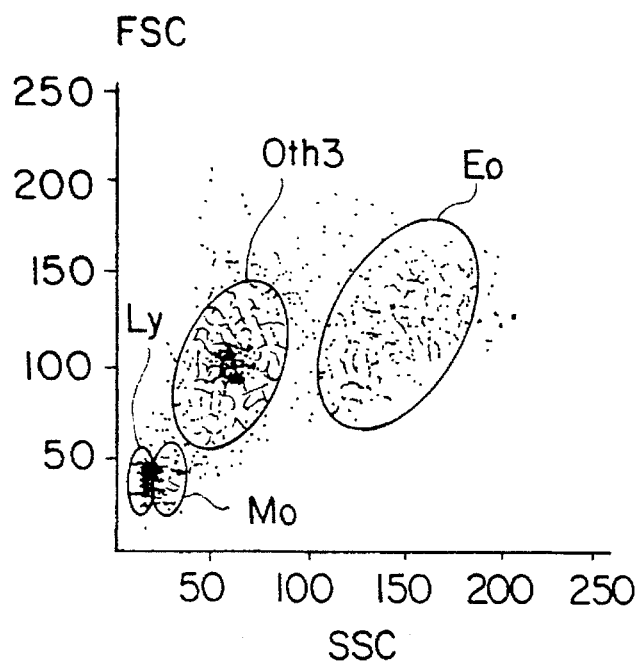

FIG. 19 is a scattergram showing the relationship between the intensity of the side scattered light (SSC) and the intensity of the forward scattered light (FSC) when a blood sample is treated with a cationic surfactant by adding ethanol (100 ml/l) as an aqueous alcohol.

Figure 20:
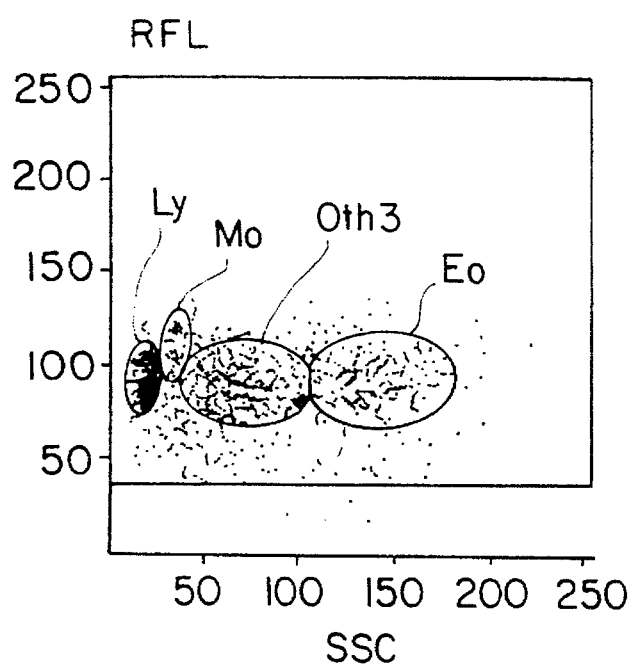

FIG. 20 is a scattergram showing the relationship between the intensity of the side scattered light (SSC) and the intensity of the red fluorescence light (RFL) when a blood sample is treated with a cationic surfactant by adding ethanol (200 ml/l) as an aqueous alcohol.

Figure 21:
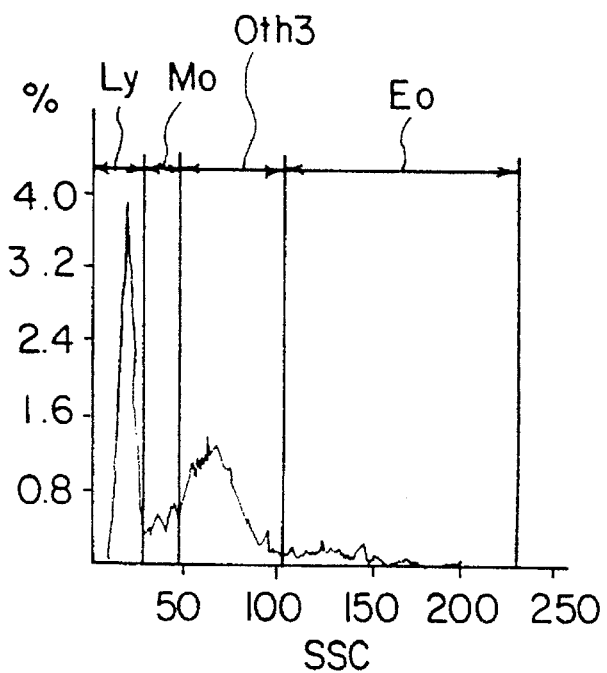

FIG. 21 is a histogram of the side scattered light when a blood sample is treated with a cationic surfactant by adding ethanol as an aqueous alcohol (200 ml/l).

Figure 22:
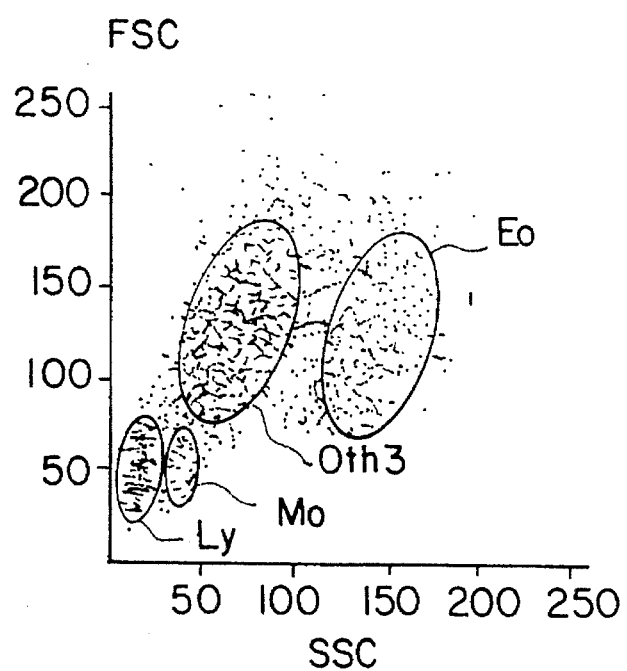

FIG. 22 is a scattergram showing the relationship between the intensity of the side scattered light (SSC) and the intensity of the forward scattered light (FSC) when a blood sample is treated with a cationic surfactant by adding ethanol (200 ml/l) as an aqueous alcohol.

Figure 23:
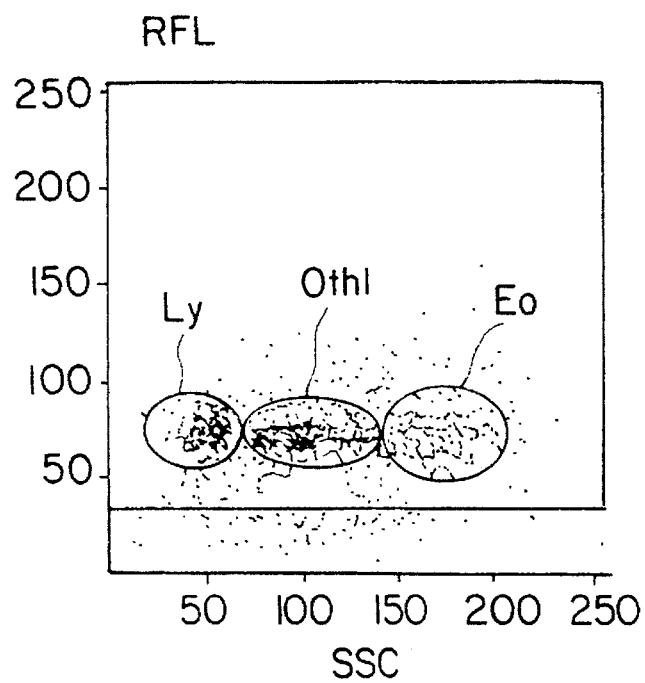
Figure 24:
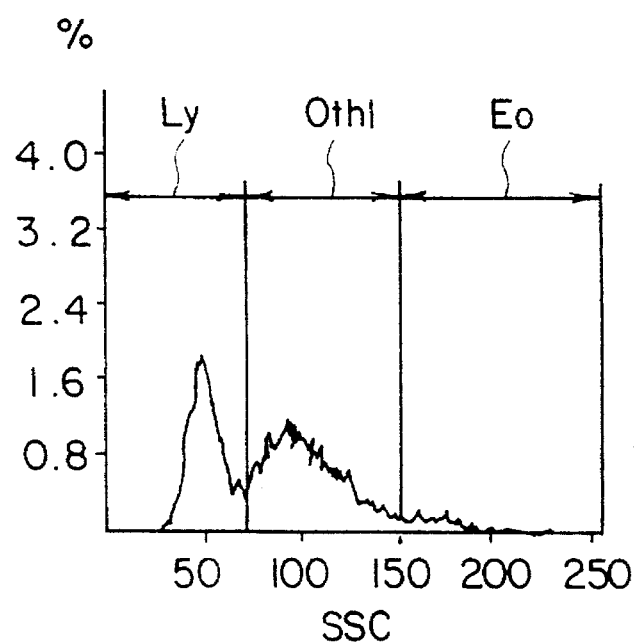

FIG. 23 is a scattergram showing the relationship between the intensity of the side scattered light (SSC) and the intensity of the red fluorescence light (RFL) when a blood sample is treated with a cationic surfactant by adding ethanol (400 ml/l) as an aqueous alcohol, FIG. 24 is a histogram of the side scattered light when a blood sample is treated with a cationic surfactant by adding ethanol (400 ml/l) as an aqueous alcohol.

Figure 25:
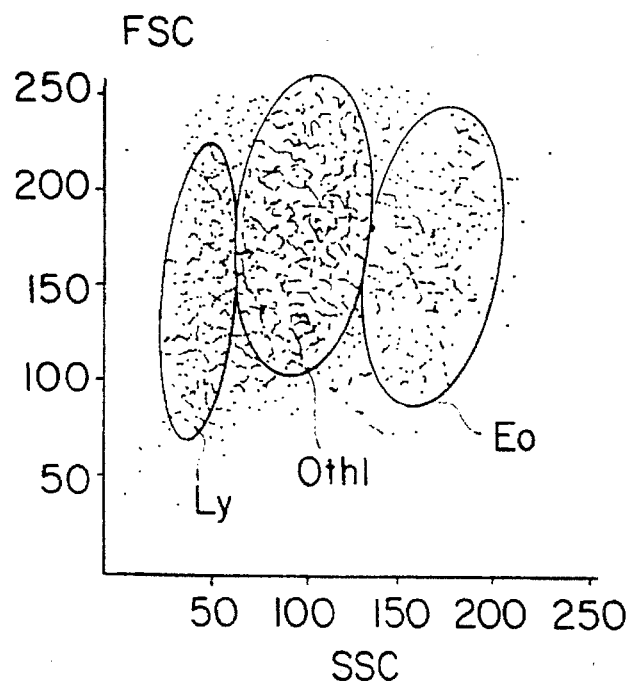

FIG. 25 is a scattergram showing the relationship between the intensity of the side scattered light (SSC) and the intensity of the forward scattered light (FSC) when a blood sample is treated with a cationic surfactant by adding ethanol (400 ml/l as an aqueous alcohol.

Figure 26:
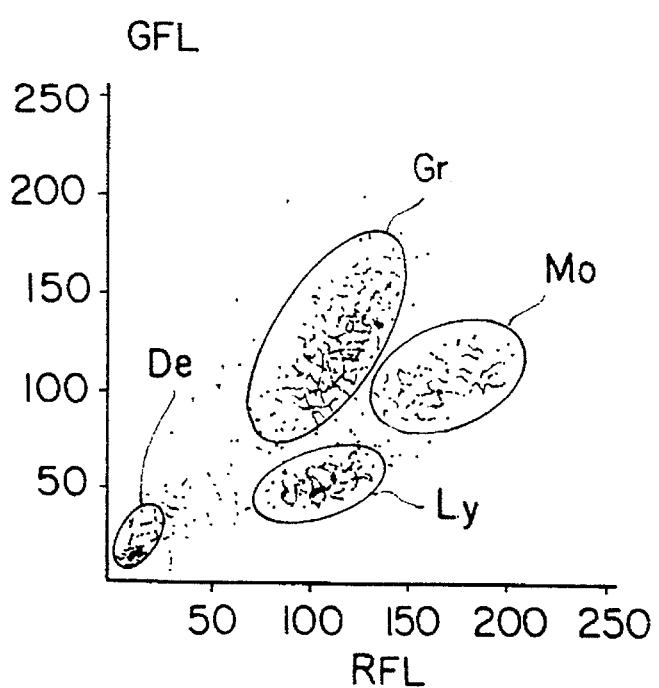

FIG. 26 is a scattergram showing the relationship between the intensity of the red fluorescence light (RFL) and the intensity of the green fluorescence light (GFL) when a venous blood sample of normal subjects is treated with the reagent composition of Example 4.

Figure 27:
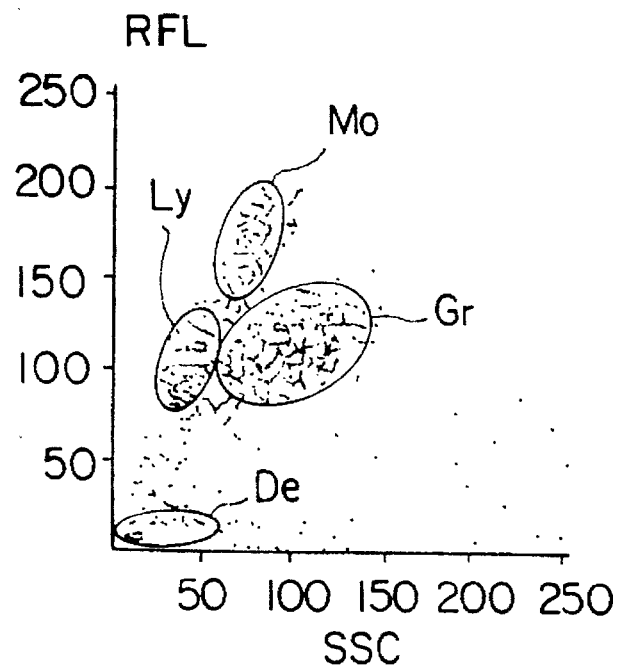

FIG. 27 is a scattergram showing the relationship between the intensity of the side scattered light (SSC) and intensity of the red fluorescence light (RFL) when a venous blood sample of normal subjects is treated with the reagent composition of Example 4.

Figure 28:
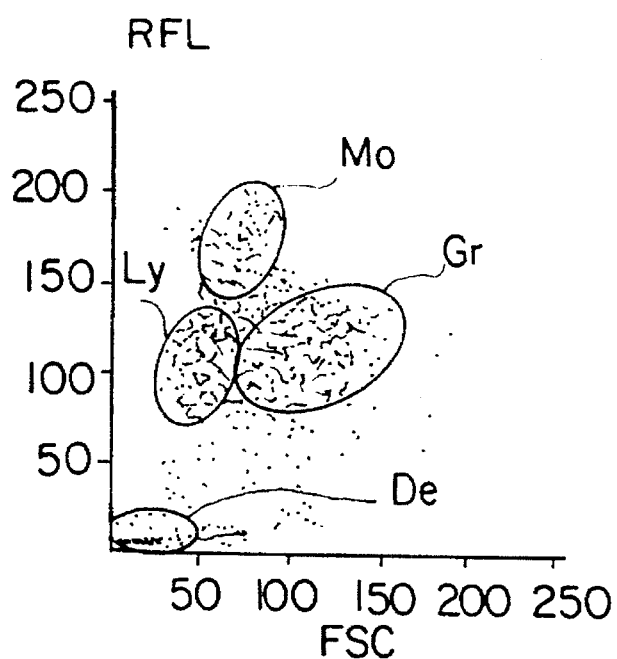

FIG. 28 is a scattergram showing the relationship between the intensity of the forward scattered light (FSC) and the intensity of the red fluorescence light (RFL) when a venous blood sample of normal subjects is treated with the reagent composition of Example 4.

Figure 29:
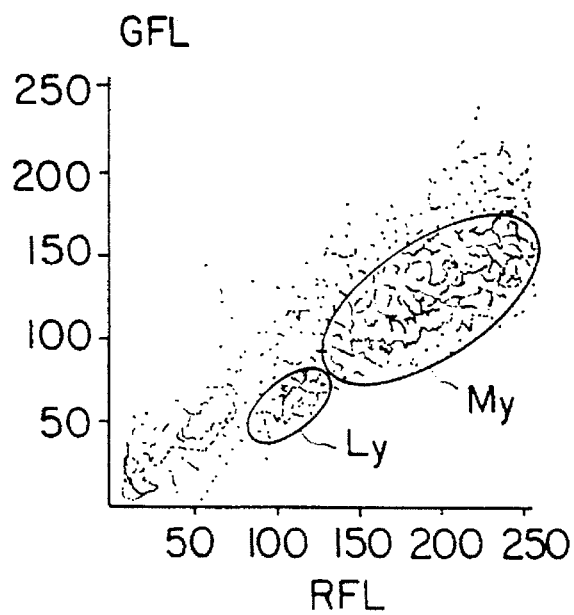

FIG. 29 is a scattergram showing the relationship between the intensity of the red fluorescence (RFL) and the intensity of the green fluorescence light (GFL) when a venous blood sample of a patient with acute myelocytic leukemia is treated with the reagent composition of Example 4.

Figure 30:
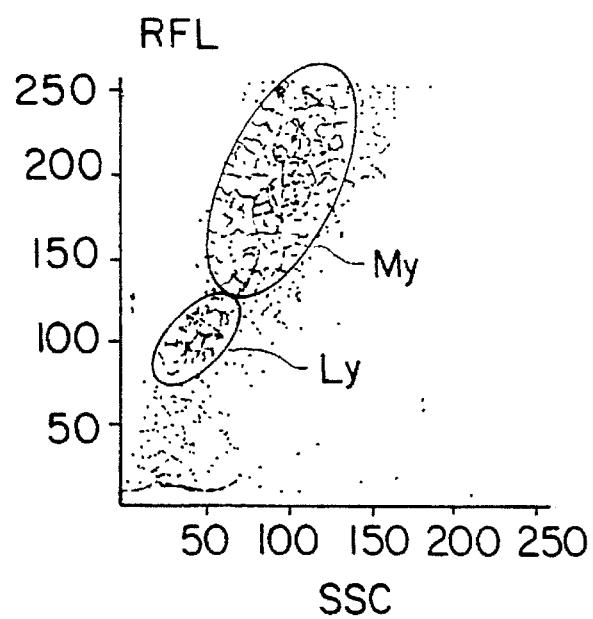

FIG. 30 is a scattergram showing the relationship between the intensity of the side scattered light (SSC) and the intensity of the red fluorescence light (RFL) when a venous blood sample of a patient with acute myelocytic leukemia is treated with the reagent composition of Example 4.

Figure 31:
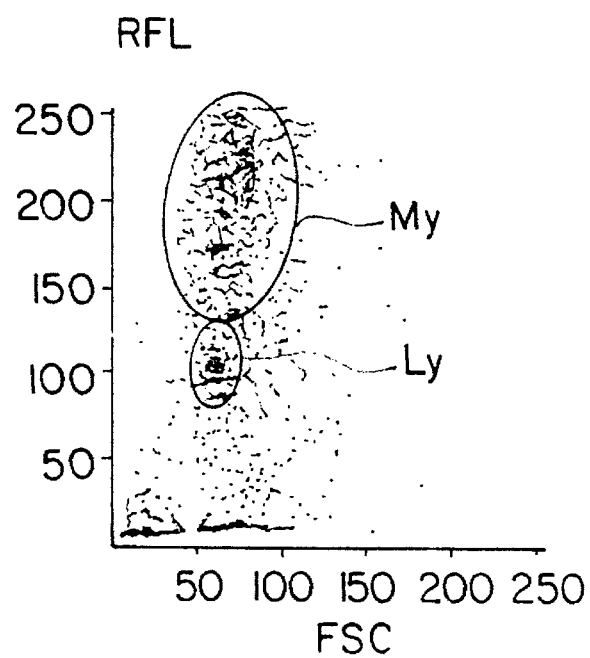

FIG. 31 is a scattergram showing the relationship between the intensity of the forward scattered light (FSC) and the intensity of the red fluorescence light (RFL) when a venous blood sample of a patient with acute myelocytic leukemia is treated with the reagent composition of Example 4.

Figure 32:
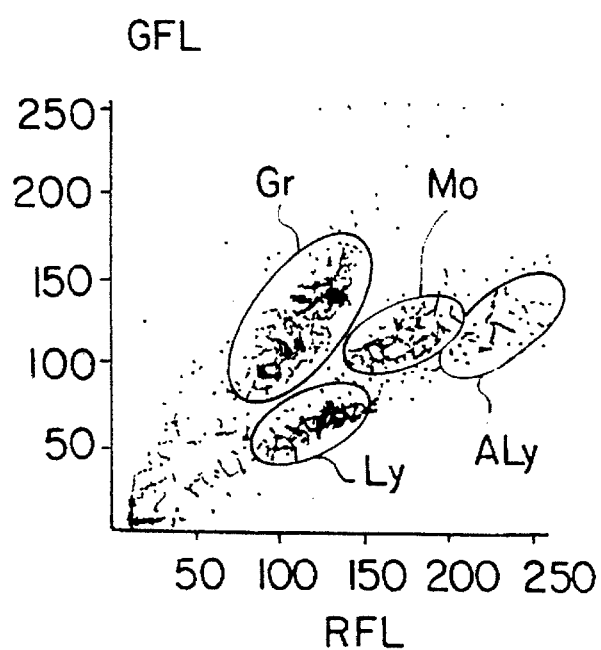

FIG. 32 is a scattergram showing the relationship between the intensity of the red fluorescence light (RFL) and the intensity of the green fluorescence light (GFL) when subjects with atypical lymphocytes is treated with the reagent composition of Example 4.

Figure 33:
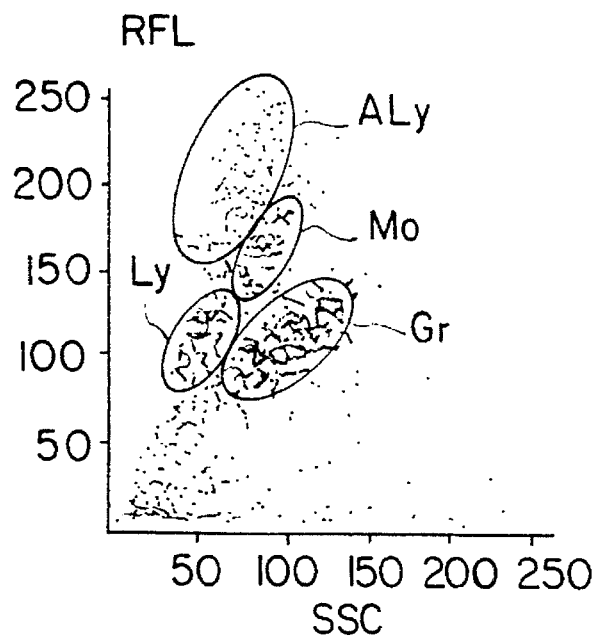

FIG. 33 is a scattergram showing the relationship between the intensity of the side scattered light (SSC) and the intensity of the red fluorescence light (RFL) when subjects with atypical lymphocytes is treated with the reagent composition of Example 4.

Figure 34:
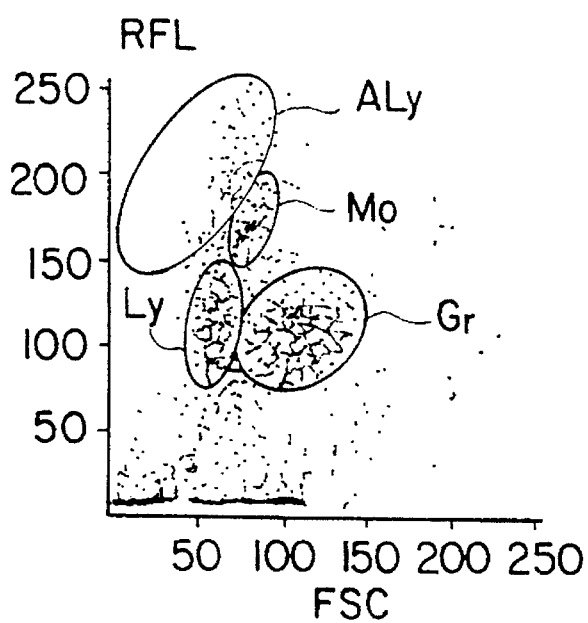

FIG. 34 is a scattergram showing the relationship between the intensity of the forward scattered light (FSC) and the intensity of the red fluorescence light (RFL) when subjects with atypical lymphocytes is treated with the reagent composition of Example 4.

Figure 35:
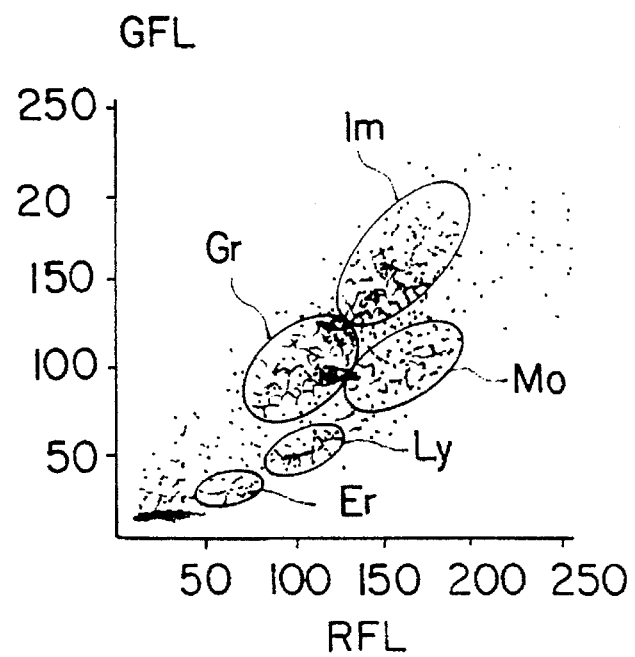

FIG. 35 is a scattergram showing the relationship between the intensity of the red fluorescence light (RFL) and the intensity of the green fluorescence light (GFL) when subjects with erythroblast and immature granulocytes is treated with the reagent composition of Example 4.

Figure 36:
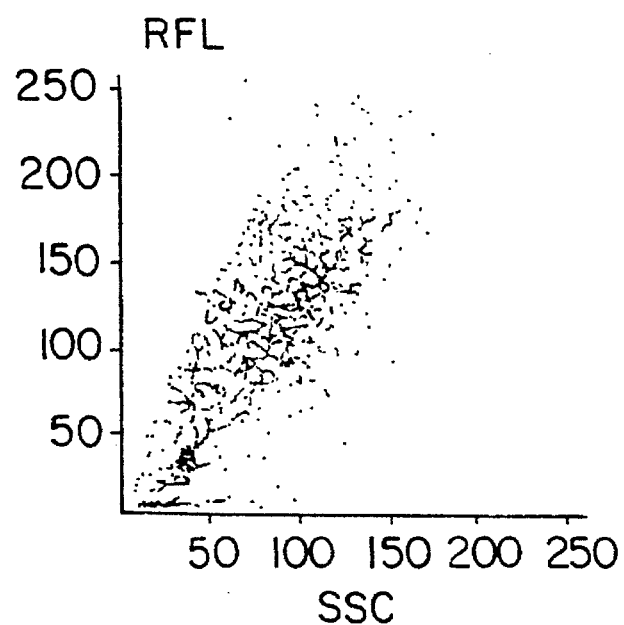

FIG. 36 is a scattergram showing the relationship between the intensity of the side scattered light (SSC) and the intensity of the red fluorescence light (RFL) when subjects with erythroblast and immature granulocytes is treated with the reagent composition of Example 4.

Figure 37:
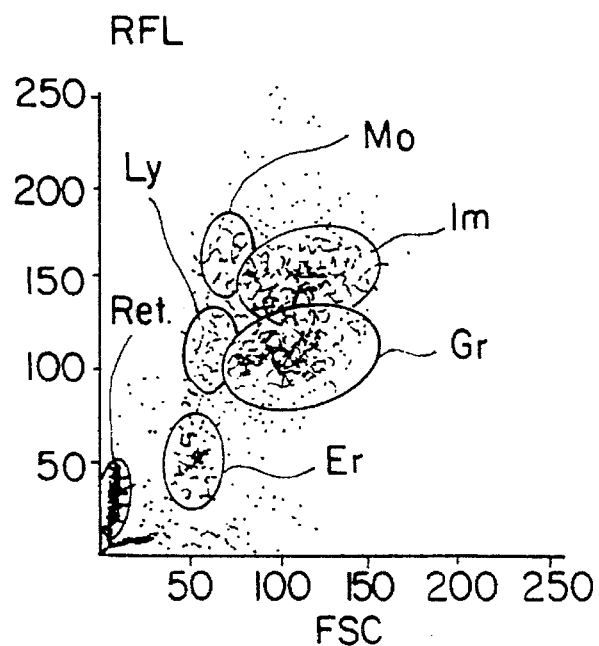

FIG. 37 is a scattergram showing the relationship between the intensity of the forward scattered light (FSC) and the intensity of the red fluorescence light (RFL) when subjects with erythroblast and immature granulocytes is treated with the reagent composition of Example 4.

Figure 38:
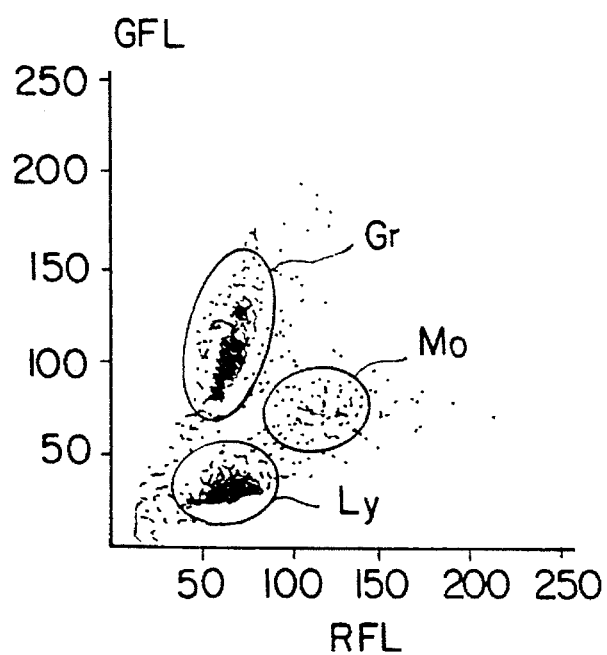

FIG. 38 is a scattergram showing the relationship between the intensity of the red fluorescence light (RFL) and the intensity of the green fluorescence light (GFL) when a venous blood sample of normal subjects is treated with the reagent composition of Example 5.

Figure 39:
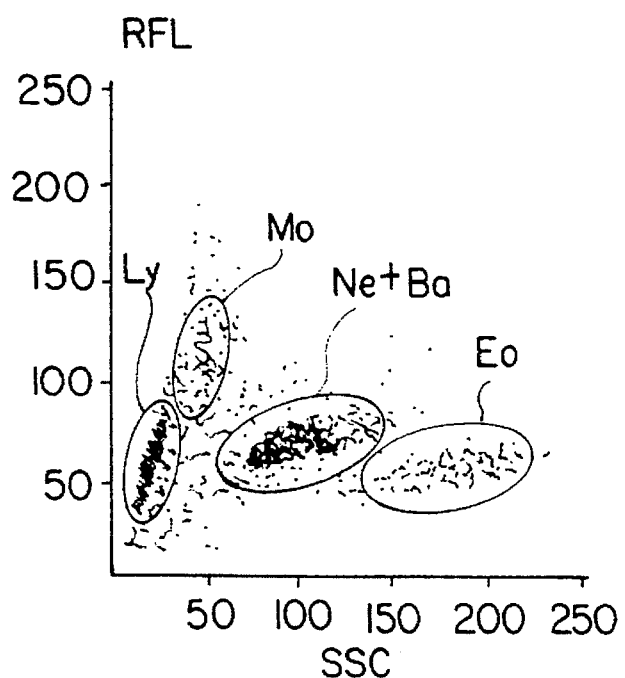

FIG. 39 is a scattergram showing the relationship between the intensity of the side scattered light (SSC) and the intensity of the red fluorescence light (RFL) when a venous blood sample of normal subjects is treated with the reagent composition of Example 5.

Figure 40:
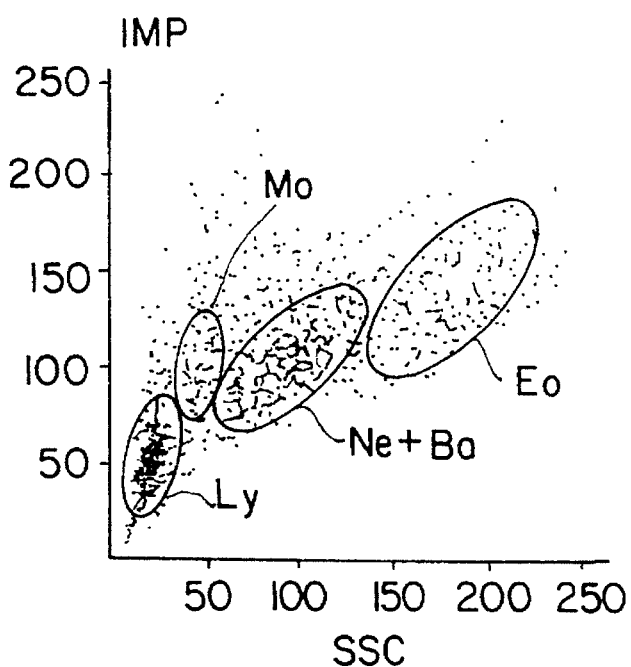

FIG. 40 is a scattergram showing the relationship between the intensity of the side scattered light (SSC) and impedance signal (IMP) when a venous blood sample of normal subjects is treated with the reagent composition of Example 5.

Figure 41:
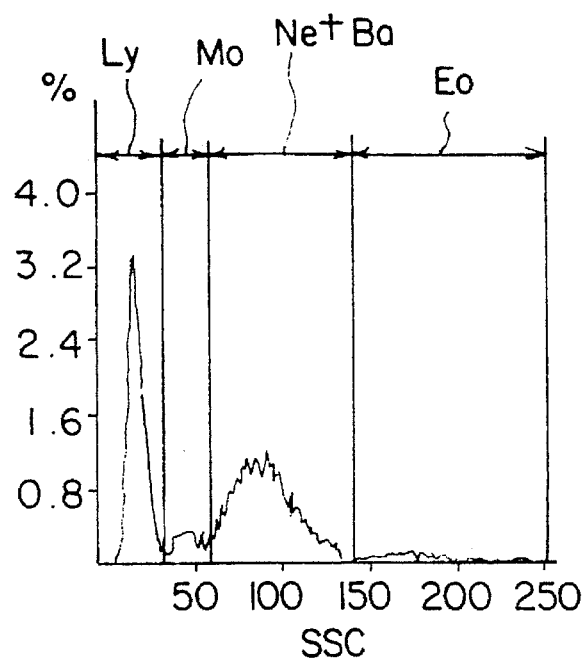

FIG. 41 is a histogram of the side scattered light when a venous blood sample of normal subjects is treated with the reagent composition of Example 5.

Figure 42:
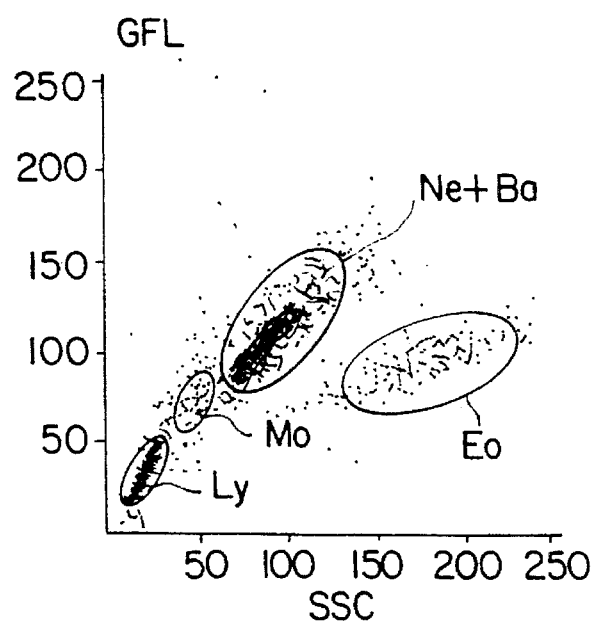

FIG. 42 is a scattergram showing the relationship between the intensity of the side scattered light (SSC) and the intensity of the green fluorescence light (GFL) when a venous blood sample of normal subjects is treated with the reagent composition of Example 5.

Figure 43:
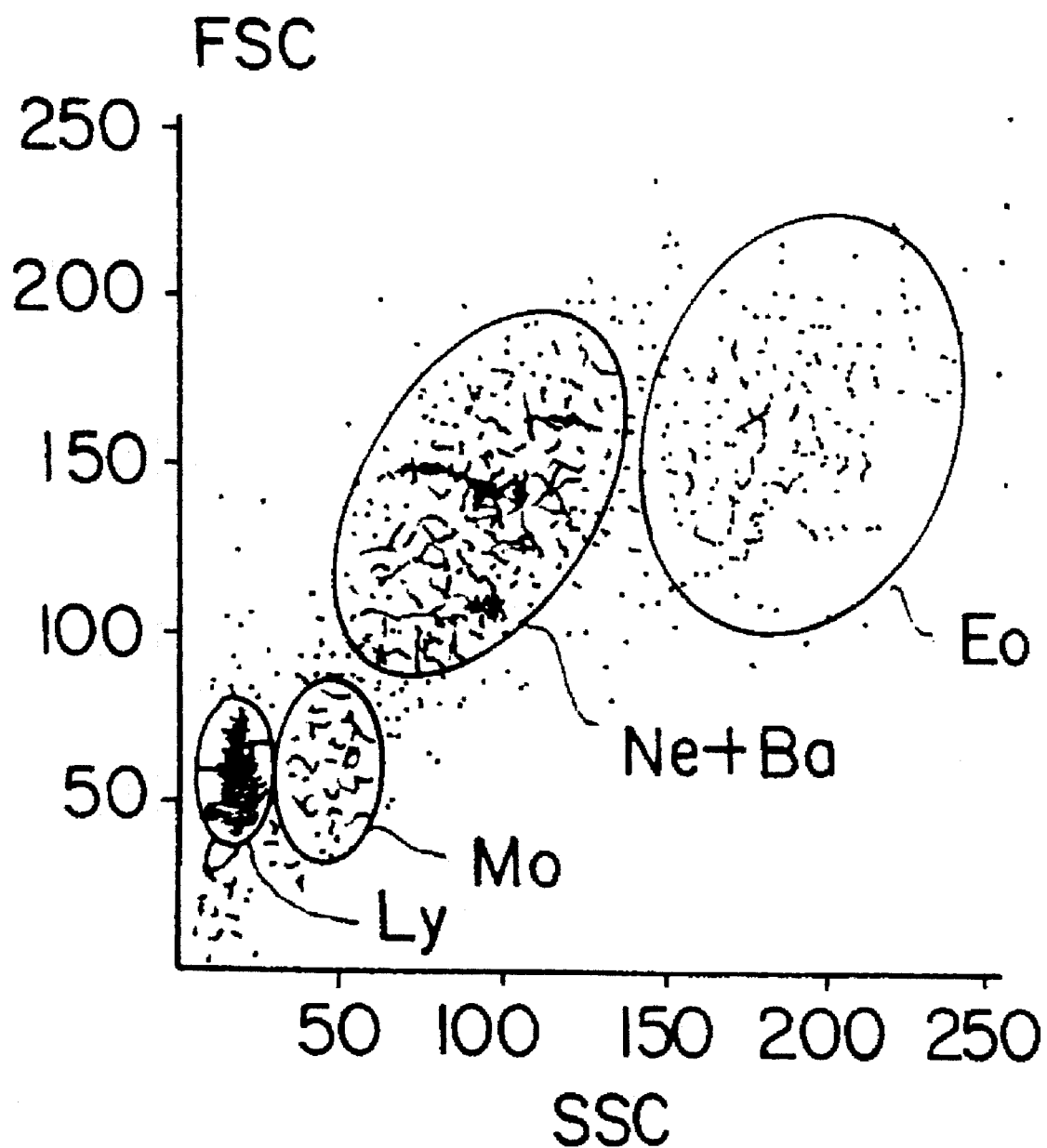

FIG. 43 is a scattergram showing the relationship between the intensity of the side scattered light (SSC) and the intensity of the forward scattered light (FSC) when a venous blood sample of normal subjects is treated with the reagent composition of Example 5.

Figure 44:
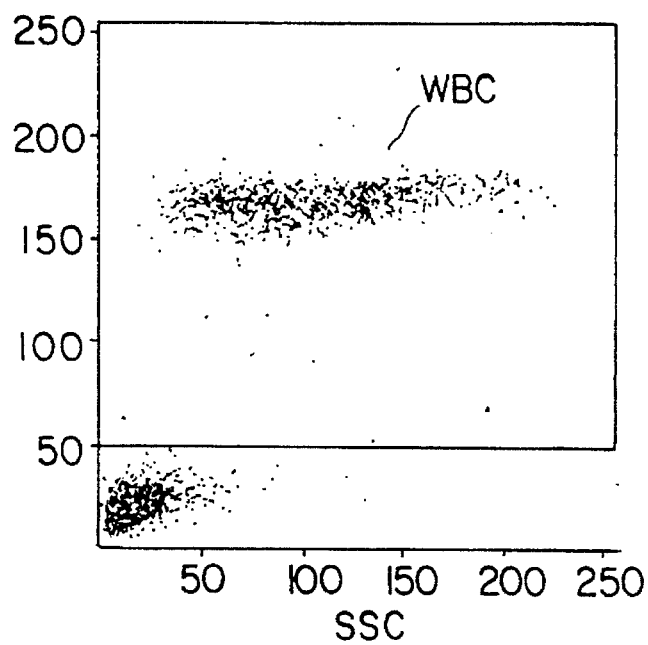

FIG. 44 is a scattergram showing the relationship between the intensity of the side scattered light (SSC) and the intensity of the red fluorescence light (RFL) when a blood sample is treated with the reagent composition of Reference Example 1.

Figure 45:
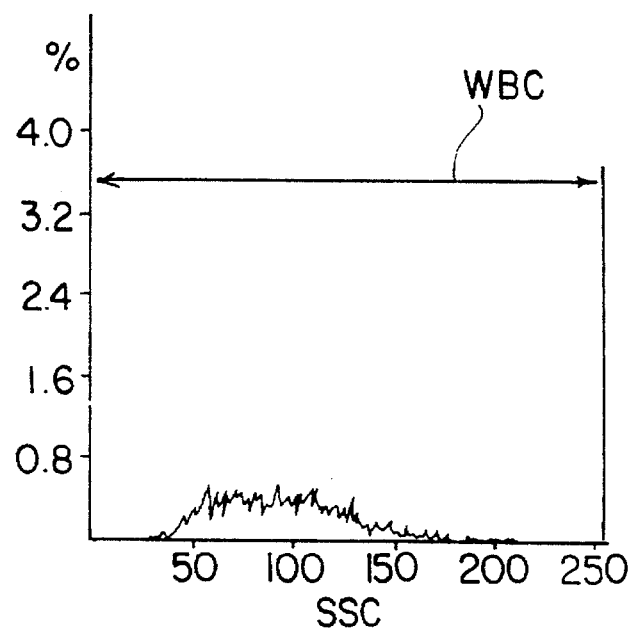

FIG. 45 is a histogram of the side scattered light when a blood sample is treated with the reagent composition of Reference Example 1.

Figure 46:
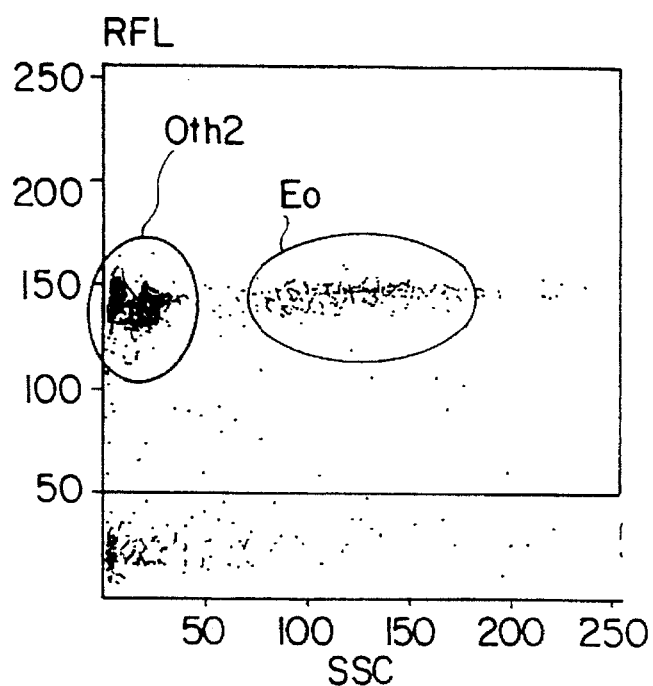

FIG. 46 is a scattergram showing the relationship between the intensity of the side scattered light (SSC) and the intensity of the red fluorescence light (RFL) when a blood is treated with the reagent composition of Reference Example 2.

Figure 47:
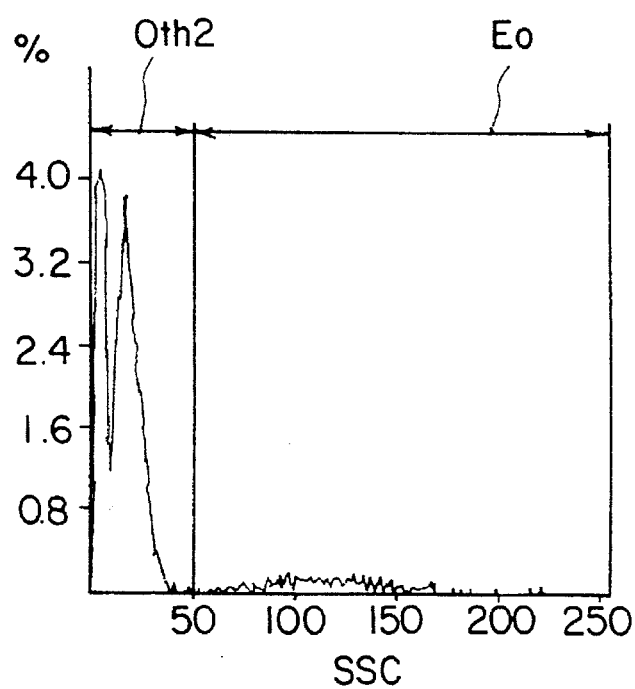

FIG. 47 is a histogram of the side scattered light when a blood sample is treated with the reagent composition of Reference Example 2.

DETAILED DESCRIPTION OF THE INVENTION

A blood sample used for the pretreatment method for blood analysis of the present invention means a sample derived from blood of a human being or animals and may be bone marrow fluid. The blood sample must contain leukocytes. However, upon circumstances, the sample may be used after having removing erythrocytes and blood platelets. According to the method of the present invention, leukocytes can be selectively classified and counted by treating the whole blood sample without removing erythrocyte and blood platelet cells. The blood sample is usually treated with an anticoagulant before applying the method.

In the present invention, an aqueous solution comprising at least one surfactant selected from the group consisting of a cationic surfactant is used and amphoteric surfactant. Preferably, the aqueous solution of the present invention contains the surfactant dissolved in an aqueous solvent, preferably water.

Preferable examples of the cationic surfactants are quaternary ammonium salt type surfactant or pyridinium salt type surfactant. Specifically, the quaternary ammonium salt type surfactant can be represented by the formula (I):

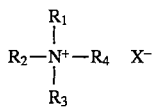

where $R_1$, $R_2$ and $R_3$ are independently a hydrogen atom, a $C_{1-8}$ alkyl or a $C_{6-8}$ aralkyl group; $R_4$ is a $C_{8-18}$ alkyl group, a $C_{8-18}$ alkenyl or a $C_{6-8}$ aralkyl group; and X is an anion. Preferable examples of the $C_{1-8}$ alkyl or $C_{6-8}$ aralkyl group represented by $R_1$, $R_2$ and $R_3$ are methyl, ethyl, octyl, heptyl, hexyl and benzyl group, among which a $C_{1-3}$ alkyl group such as a methyl and ethyl group is more preferable. Preferable examples of the $C_{8-18}$ alkyl group, $C_{8-18}$ alkenyl group or $C_{6-18}$ aralkyl group represented by $R_4$ are octyl, decyl, dodecyl, tetradecyl and benzyl group.

The pyridinium salt type surfactant can be represented by the formula (II):

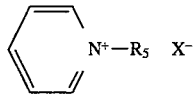

where $R_5$ is a $C_{8-18}$ alkyl group and X is an anion group. Preferable examples of the $C_{8-18}$ alkyl group represented by $R_5$ are a $C_{10-18}$ straight chain alkyl group such as decyl, dodecyl and tetradecyl group. Specific examples of these cationic surfactants are lauryltrimethylammonium chloride, myristyltrimethylammonium chloride, cetyltrimethylammonium chloride, cetyldimethylethylammonium chloride and benzyldimethylcetylammonium chloride.

The amphoteric surfactant includes a betaine type surfactant having the formula (III):

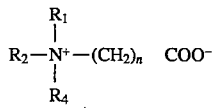

where $R_1$ and $R_2$ are independently a hydrogen atom, a $C_{1-8}$ alkyl or a $C_{6-8}$ aralkyl group; $R_4$ is a $C_{8-18}$ alkyl group, a $C_{8-18}$ alkenyl group and a $C_{6-18}$ aralkyl group; and n is 1 or 2. Specific examples of the betaine type surfactant include lauryldimethylaminoacetic betaine and stearyldimethylaminoacetic betaine.

In the present invention, the aqueous solution comprising the cationic or amphoteric surfactant is used at an concentration that does not destroy the whole cell membrane of leukocytes but is sufficient to damage the cell membrane so as to make it permeable. It is preferable to use the surfactant at a concentration of in the range of about 30 to 5,000 mg/l, preferably about 50 to 2,000 mg/l, more preferably about 50 to 1,500 mg/l.

If the surfactant is used in an excess amount, the labeling function of some labeling substances is inhibited by the surfactants. Also, use of the surfactant at a higher concentration than the above upper limit lyses cells and results in naked nuclei, so that an optical difference is hardly measured by using a scattered light. The aqueous surfactant solution is preferably used at 2–200 volumes per one volume of the blood sample. It is not recommended to dilute the blood sample too much with the surfactant solution because components of blood other than leukocytes, for example erythrocytes, are not lysed, thereby causing a difficulty of the measurement.

The labeling substance usable in the present invention is any substance that can pass through the damaged cell membrane of the leukocyte and thus be combined with components contained therein. For example, a fluorescence dye is preferably used when a flow cytometer is used for measuring a general fluorescence light and scattered light. In the case of using a flow cytometer for measuring absorbency, a dye other than a fluorescence dye can be used. Alternatively, a substance which can generate a dye by reacting with cell components is also preferably used. Such labeling substances are known in publications related to flow cytometry.

In this specification, the phrase "combined with cell components" means ionic bonding between the cell components and the labeling substance or covalent bonding between proteins (amino group) contained in the cell and the labeling substance.

As examples of the labeling substances that can be combined with the cell nucleus (DNA), ethidium bromide (EB) and propidium iodide (PI) are well known. In addition, most basic dyes can be used for staining nuclei. Examples of the labeling substances that can be combined with RNA include Pyronin Y, Acridine Orange, Tiazole Orange, Acridine Orange 10 dodecyl bromide and Auramine-O. Alternative examples of the labeling substances that can react with proteins in the cell (amino group) include fluorescein isothiocyanate (FITC) and 7-chloro-4-nitrobenzoxazole (NBD-Cl).

As described above, dyes other than those generally used for a flow cytometer can be used. For example, a dye generally used for measuring electric potential of a cell membrane such as 3,3'-dihexyloxacarbocyanine (DiOC6(3)) can be also used because such a dye passes through a cell membrane so easily that it can stain components contained in the cell such as granules.

According to the present invention, a distinctive stain is exhibited by staining the treated cells, which is different from the stain exhibited by staining normal alive cells or fixed cells. Therefore, the present invention can be also used in order to develop usage of dyes which have been used for staining cells for the purpose other than classifying and counting leukocytes, or to examine a possibility of usage of dyes which have not been used for staining cells.

The labeling substance is added at a concentration of 1 to 500 mg/l, preferably about 1 to 200 mg/l.

As an applied example of the present invention, nucleate and anucleate cells are distinguished by treating the cells with a cationic or amphoteric surfactant, followed by staining with the labeling substance capable of combining with cell nucleus (DNA), for example, DNA stains such as propidium iodide and ethidium bromide. In addition, in the case where a flow cytometer capable of measuring fluorescence or scattered light is used, fluorescent basic dyes are suitably used as the labeling substance.

In the present invention, when the surfactant and labeling substance are added to the blood sample, the pH range of the solution is preferably adjusted to pH 3.0–11.0, more preferably from pH 4.0 to 11.0. In case of detecting eosinophils by using side scattered light, it is preferable to be at pH 5.0–11.0. Further, if the formation of a bonding between the labeling substance and cell components or the acting of the surfactant on cells depends on pH value, a suitable buffer may be added for maintaining desired pH.

The method for treating a blood sample with the surfactant and the labeling substance is not specifically limited, but is conducted by a known method. For example, an aqueous reagent solution comprising the surfactant and the labeling substance is mixed with the blood sample which is pretreated with an anticoagulant. In this case, the pH of the aqueous reagent solution may be adjusted to the above range by adding a buffer. The buffer may be added simultaneously to the reaction system. The method of the present invention can be generally carried out at a temperature from room temperature to a slightly elevated temperature, for example about 10° to 50° C. The reaction according to the method of the present invention generally proceeds very fast, for example, being complete in 5 to 30 seconds. Therefore, it is found that the present invention is suitably adapted for classifying and counting leukocytes by a high speed automatic analysis device.

In the present invention, a nonionic surfactant may be added to the aqueous reagent solution of the cationic or amphoteric surfactant and the labeling substance. Preferably, the nonionic surfactant comprises at least one selected from polyoxyethylene glycol type agents having the formula:

wherein $R_6$ is a $C_{8-22}$ alkyl group or a $C_{8-22}$ alkenyl group, $R_7$ is —O—, —COO—, or

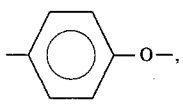

and n is an integer of 10 or more.

The nonionic surfactant of this type is economically advantageous because it is available at a low price. Among them, the nonionic surfactant of n (addition molar number) being 10 or more are particularly preferable because of water-solubility and less cytotoxicity. Specific examples of the polyoxyethyleneglycol surfactants are 20 molar addition products of polyoxyethyleneglycol nonylphenyl ether, 30 molar addition products of polyoxyethyleneglycol cetyl ether, and 20 molar addition products of polyoxyethyleneglycol oleyl ether. Further, it is possible to use other nonionic surfactants than the above mentioned polyoxyethyleneglycol type, e.g., those having HLB (hydrophite-lipopophile balance) value of 13 or more such as TWEEN™ type (polyoxyethylene sorbitan alkylate surfactants).

The amount of the above nonionic surfactant is preferred to be used at a concentration of 100 to 10,000 mg/l, more preferably, at a concentration of 100 to 5,000 mg/l, which varies depending upon the kind of the cationic or amphoteric surfactant and other conditions.

The mechanism of the function of the nonionic surfactant is not made clear, but is considered to be that the nonionic surfactant is combined with the surface of the cell to control the acting of the ionic surfactant toward the cell membrane, thereby inhibiting the lysis of cell components with the ionic surfactants. For example, the use of the ionic surfactant associated with the nonionic surfactant is preferable when the ionic surfactant has so potent a lysing activity that leukocytes are unnecessarily damaged. The nonionic surfactant also will act to accelerate the lysis of erythrocytes, which causes a problem in the case of measuring leukocytes contained in a blood sample. Further, it can act to solubilize substances which are precipitated from a reaction solution by neutralization of anionic substances included in cell components or others of the blood sample, with the cationic surfactant. In addition, it can exert to inhibit aggregation of erythrocytes which remain as ghosts without their complete lysing, which will occur in the case where erythrocytes are rich as in a test sample of blood product and the dilution of a said test sample with the aqueous reagent solution is obliged to be low. In such case where the dilution ratio of the aqueous reagent solution must be low, the nonionic surfactant is effectively used; otherwise it is not necessary.

Alternatively, the nonionic surfactant generally shows a solubility effect for a water-insoluble labeling substance, which is a merit of increasing the number of the available labeling substances.

According to the method of the present invention, a water soluble alcohol can be further contained in the aqueous reagent solution when the blood sample is treated with the aqueous reagent solution of at least one cationic or amphoteric surfactant. Examples of the water soluble alcohols include a water soluble aliphatic alcohol having 2 to 5 carbon atoms such as ethyl alcohol, propyl alcohol, isopropyl alcohol and t-butyl alcohol, among which a branched chain alcohol such as isopropyl alcohol or t-butyl alcohol is preferable. The similar effect can be exhibited by using an alkoxyalcohol such as methoxyethanol or an aromatic alcohol such as phenethyl alcohol.

The concentration of the water soluble alcohol to be added depends on the type of the cationic or amphoteric surfactant or other conditions. In case of using ethyl alcohol or isopropyl alcohol, it is preferably used at a concentration of 50 to 400 ml/l or 25 to 200 ml/l, using half that concentration of each alcohol having one extra carbon atom.

The water soluble alcohol acts to selectively enhance the function of the ionic surfactant, thereby damaging cell membranes at a lower concentration of the ionic surfactant. Also, it denatures proteins contained in cells and makes the proteins to be insoluble. Accordingly, the use of the water soluble alcohol is effective to minimize the loss of cytoplasms and granules and to optimize the degree of damage of the cell membrane. Therefore, the water soluble alcohol also acts for maintaining the effect of obtaining an optical difference measured by scattered light and the like. Further, the water soluble alcohol has an effect to facilitate the lysis of erythrocytes.

In using the blood sample subjected to the method of the present invention, the labeled cells can be easily classified and counted, for example, by an optical means such as flow cytometer or the like, or other known means.

From another aspect of the present invention, it provides a blood analysis reagent suitable for applying the method of the present invention. The preferred reagent used for the present invention is as follows:

(a) a reagent comprising:
about 50 to 5,000 mg/l of a cationic or amphoteric surfactant,
about 1 to 200 mg/l of a labeling substance,
and an aqueous medium of water or water soluble alcohol to be balanced to one liter.

(b) a reagent comprising:
about 50 to 5,000 mg/l of a cationic or amphoteric surfactant,
about 100 to 10,000 mg/l of a nonionic surfactant,
about 1 to 200 mg/l a labeling substance, and
an aqueous medium of water, or water and water soluble alcohol to be balanced to one liter.

(c) a reagent of (a) and (b) above, in which a buffer is contained to adjust the pH to pH 3.0–11.0.

The function of the ingredients of the reagent composition of the present invention is further described as follows.

The surfactant of the present invention is believed to function to remove a part of substances which constitute a cell membrane, probably lipid molecules, thereby yielding pores in cell membrane which can pass a substance which does not usually pass the membrane. This is the damage of the cell membrane. The effect of the present invention can be achieved by this function. In particular, a labeling substance such as a dye is allowed to come into a cell and rapidly combine with an intracellular component. For example, in case that the combination is formed by an ionic bone as set forth below, the labeling is complete almost instantly.

As a secondary effect, the cationic and amphoteric surfactants having a positive charge in their molecule have a function that the positive charge is ionically bound with the intracellular components having negative charge (for example, RNA with a phosphoric group, protein with a carboxyl group, and the like), whereby the intracellular components become insoluble.

The insolubilized components do not leak out from the cell even when its membrane is damaged. Moreover, the cell which accumulates the insolubilized components is prevented from leaking of most of its cytoplasm, nucleus, and granules. Therefore, an optical difference can be unexpectedly obtained by measuring the side scattered light as described hereinafter, when the reagent is suitably prepared.

EXAMPLES

Example 1: Concentration of Cationic or Amphoteric Surfactant

An aqueous solution having the following composition:

| | |
|---|---|
| HEPES-NaOH buffer (PH 7.0) | 10 mM |
| Labeling substance (Ethidium bromide (EB)) | 50 mg/l | was mixed with an aqueous solution (1 ml) comprising various surfactants and venous blood (25 µl) which was treated with an anticoagulant. The resulting solution was put into a flow cytomerter where red fluorescence light and side scattered light were measured to determine the concentration of the surfactant at which staining with EB is observed. The results are shown in Table 1.

TABLE 1

| Surface Active Agent | Concentration |
|---|---|
| Lauryltrimethylammonium chloride (LTAC) | 500 mg/l |
| Myristyltrimethylammonium chloride | 100 mg/l |
| Cetyltrimethylammonium chloride | 50 mg/l |
| Cetylpyridinium chloride | 50 mg/l |
| Lauryldimethylaminoacetic betaine (Anon BL, produced by NIHON YUSHI Co.) | 500 mg/l |
| Stearyldimethylaminoacetic betaine | 500 mg/l |
| Cetyldimethylethylammonium bromide | 50 mg/l |
| Benzyldimethylcetylammonium chloride | 50 mg/l |

As shown in Table 1, the stronger hydrophobicity a surfactant has, the lower concentration the agent is used at, the weaker the hydrophobicity of the surfactant, the higher concentration the agent is used at.

Figure 1:
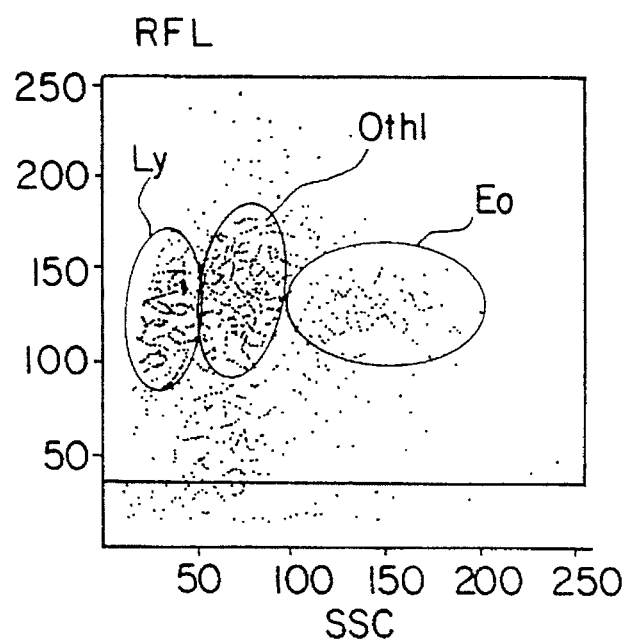
FIG. 1 is a scattergram showing the relationship between the intensity of the side scattered light (SSC) and the intensity of the red fluorescence light (RFL) when a blood sample is treated with lauryltrimethylammonium chloride as a surfactant.
Figure 2:
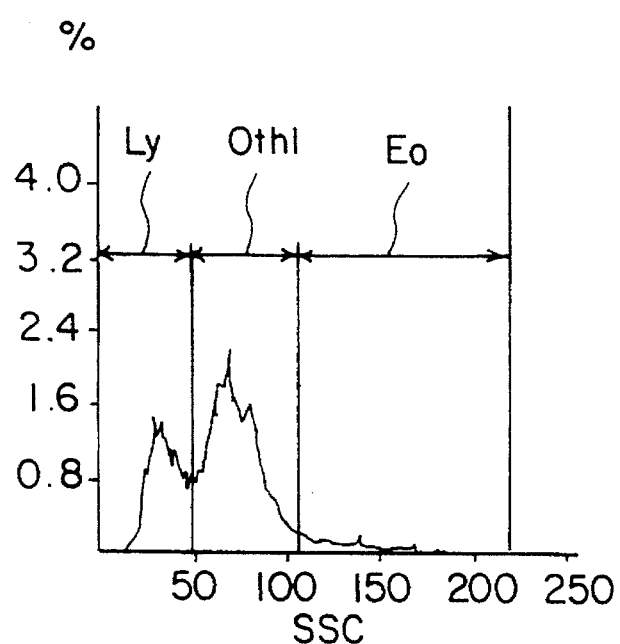
FIG. 2 is a histogram of the side scattered light when a blood sample is treated with lauryltrimethylammonium chloride as a surfactant.

FIG. 1 shows a scattergram by the side scattered light (SSC) and red fluorescence light (RFL) were measured by using lauryltrimethylammonium chloride (hereinafter referred to LTAC) as the surfactant. In FIG. 1, leukocytes can be distinguished from other blood corpuscles by the difference of red fluorescence light signals. Further, as is clearly shown from FIG. 1, lymphocytes (Ly); leukocytes other than lymphocytes ((Oth1) and eosinophils (Eo); can be classified and counted. FIG. 2 is a histogram of the side scattered light obtained by the same experiment. Similarly, lymphocytes, granulocyte Oth1 other than lymphocytes and eosinophils, and eosinophils can be classified and counted from FIG. 2.

Figure 3:
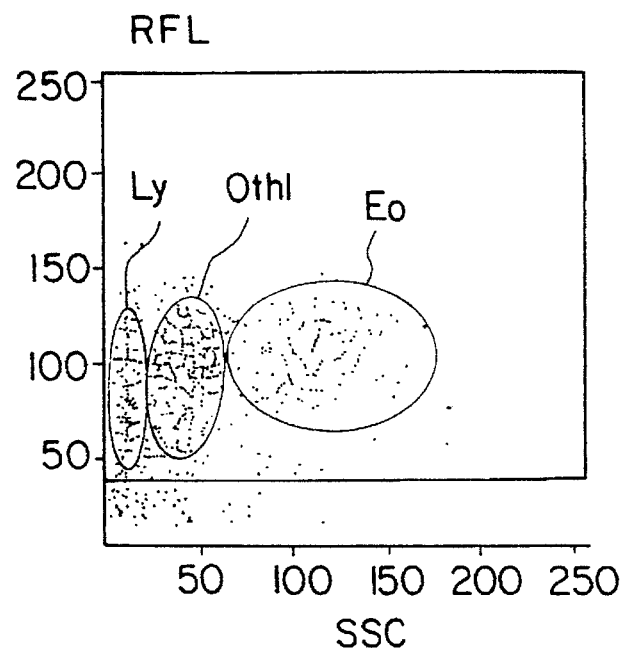
FIG. 3 is a scattergram showing the relationship between the intensity of the side scattered light (SSC) and the intensity of the red fluorescence light (RFL) when a blood sample is treated with lauryldimethylaminoacetic betaine as a surfactant.
Figure 4:
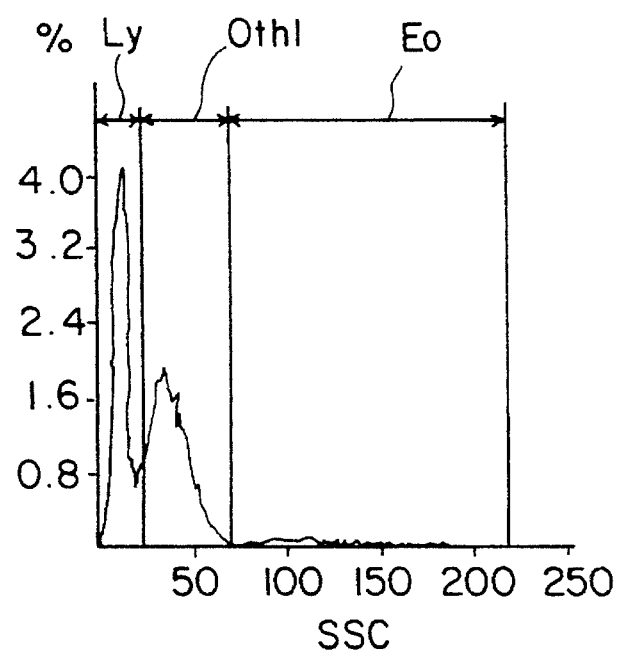
FIG. 4 is a histogram of the side scattered light when a blood sample is treated with lauryldimethylaminoacetic betaine as a surfactant.

FIGS. 3 and 4 are a scattergram and histogram in case of using lauryldimethylaminoacetic betaine (Anon BL) as the surfactant. In this case, lymphocytes (Ly); leukocytes other than lymphocytes (Oth1) and eosinophils (Eo); and can be also classified and counted.

Figure 5:
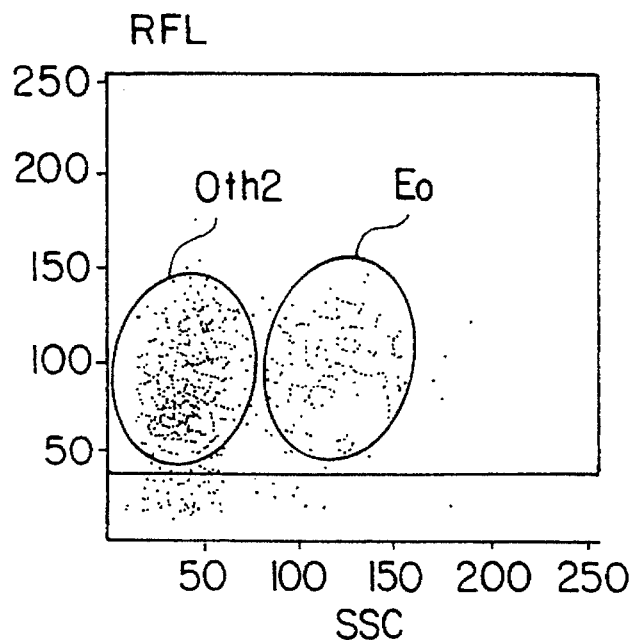
FIG. 5 is a scattergram showing the relationship between the intensity of the side scattered light (SSC) and the intensity of the red fluorescence light (RFL) when a blood sample is treated with benzyldimethylcetylammonium chloride as a surfactant.
Figure 6:
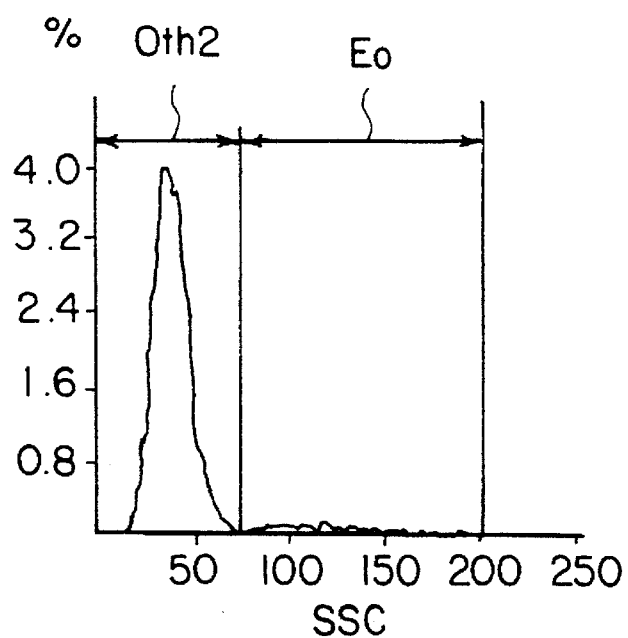
FIG. 6 is a histogram of the side scattered light when a blood sample is treated with benzyldimethylcetylammonium chloride as a surfactant.

Other surfactants having a strong lysing property classify leukocytes into 2 groups under the condition described above. For example, FIGS. 5 and 6 show the case when benzyldimethylcetylammonium chloride was used as the surfactant. It is seen from these figures that leukocytes were classified and counted only into two groups; for eosinophils (Eo) and other leukocytes (Oth2). The lysing property of the surfactants can be adjusted by adding a nonionic surfactant, thereby obtaining more detailed classification as described later.

Thus, leukocytes can be unexpectedly classified by using a reagent comprising the ionic surfactant that has been considered not to be available for generating an optical difference.

Upon observing the relationship between the surfactant and the performance of leukocyte classification, it was found that the extent of cell damage was increased in accordance with the increase of the hydrophobicity of the surfactant, resulting in difficulty in the classification. In addition, it was observed that the classification was made difficult by an increase of the concentration of the surfactants.

Example 2: Effect of Containing the Nonionic Surfactant

A reagent having the following composition was prepared.

| | |
|---|---|
| HEPES-NaOH buffer (PH 7.0) | 10 mM |
| Ethidium bromide (EB) | 50 mg/l |
| LTAC | 1,000 mg/l |
| Nonionic surfactant | 1,000 mg/l |

To the reagent (1.0 ml) having the above composition, venous blood (25 µl) which was treated with an anticoagulant was mixed. The red fluorescence light and side scattered light were measured by a flow cytometer. The results are shown in FIGS. 7 to 16.

Figure 7:
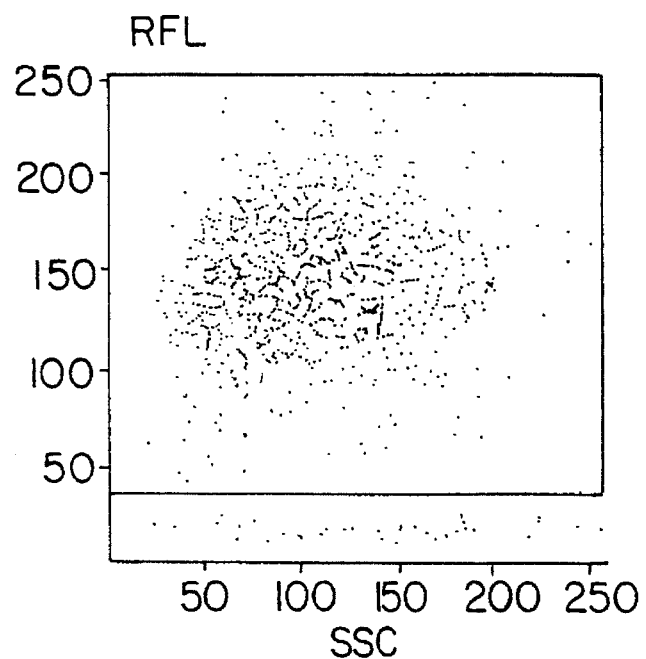
FIG. 7 is a scattergram showing the relationship between the intensity of the side scattered light (SSC) and the intensity of the red fluorescence light (RFL) when a blood sample is treated without adding a nonionic surfactant.
Figure 8:
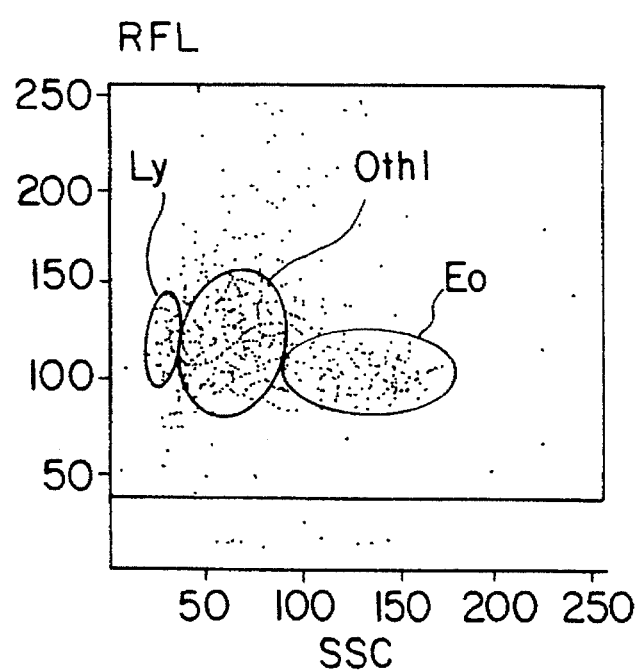
FIG. 8 is a scattergram showing the relationship between the intensity of the side scattered light (SSC) and the intensity of the red fluorescence light (RFL) when a blood sample is treated with $C_{16}H_{33}O—(CH_2CH_2O)_{10}—H$ as a nonionic surfactant.
Figure 9:
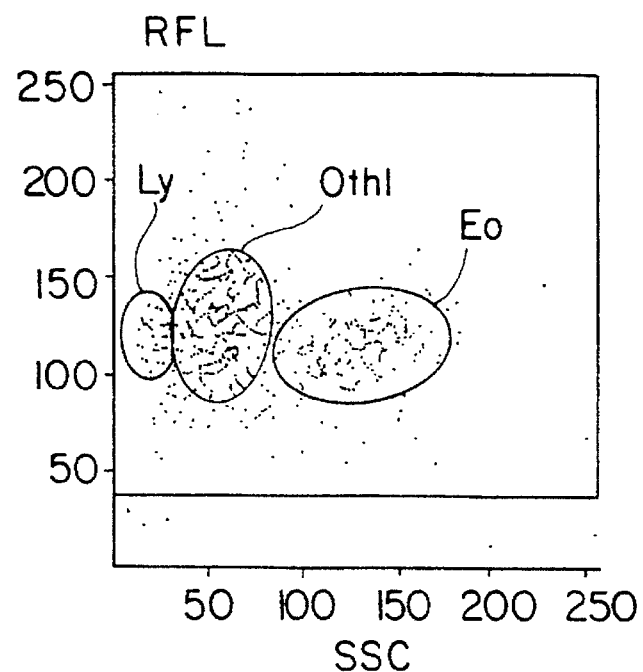
FIG. 9 is a scattergram showing the relationship between the intensity of the side scattered light (SSC) and the intensity of the red fluorescence light (RFL) when a blood sample is treated with $C_{16}H_{33}O—(CH_2CH_2O)_{20}—H$ as a nonionic surfactant.
Figure 10:
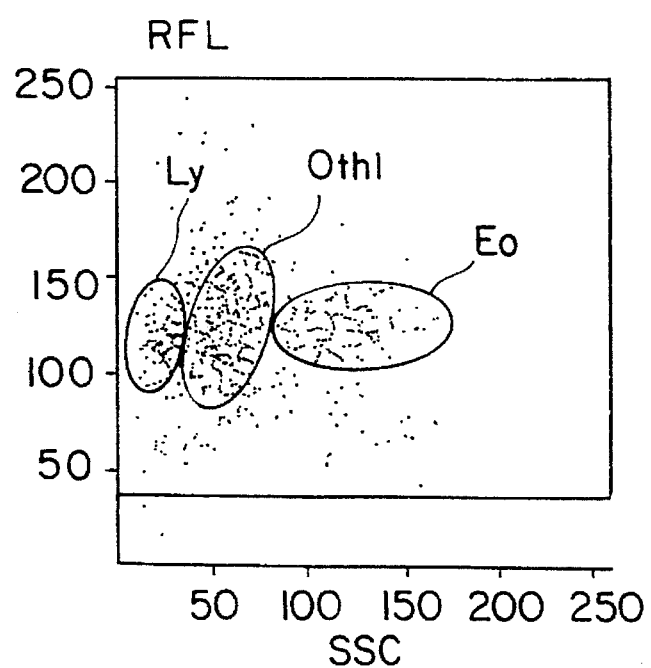
FIG. 10 is a scattergram showing the relationship between the intensity of the side scattered light (SSC) and the intensity of the red fluorescence light (RFL) when a blood sample is treated with $C_{16}H_{33}O—(CH_2CH_2O)_{30}—H$ as a nonionic surfactant.
Figure 11:
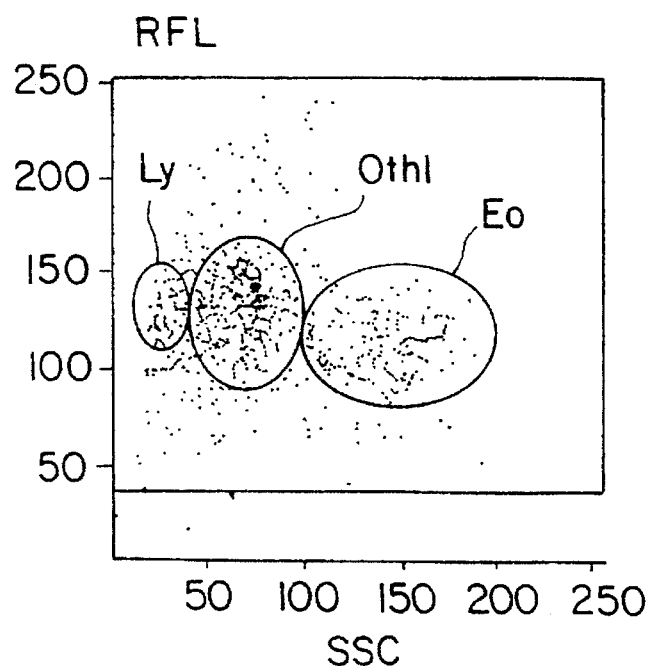
FIG. 11 is a scattergram showing the relationship between the intensity Of the side scattered light (SSC) and the intensity of the red fluorescence light (RFL) when a blood sample is treated with $C_{12}H_{25}O—(CH_2CH_2O)_{30}—H$ as a nonionic surfactant.
Figure 12:
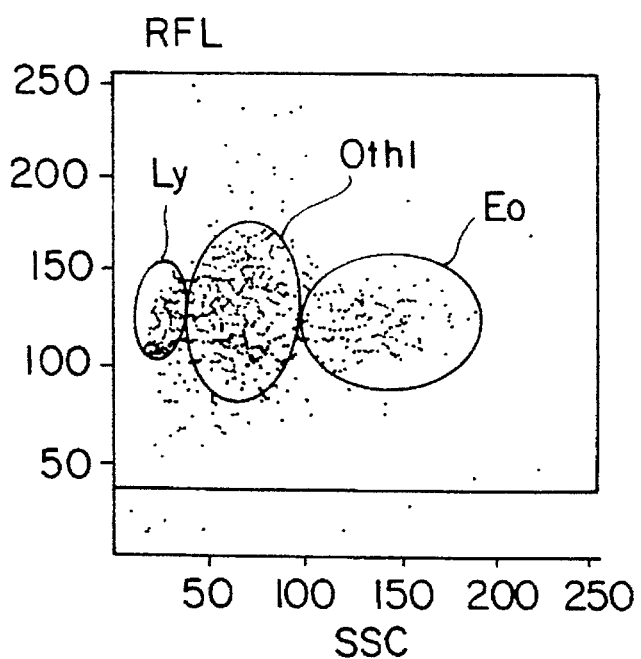
FIG. 12 is a scattergram showing the relationship between the intensity of the side scattered light (SSC) and the intensity of the red fluorescence light (RFL) when a blood is treated with $C_{18}H_{37}O—(CH_2CH_2O)_{20}—H$ as a nonionic surfactant.
Figure 13:
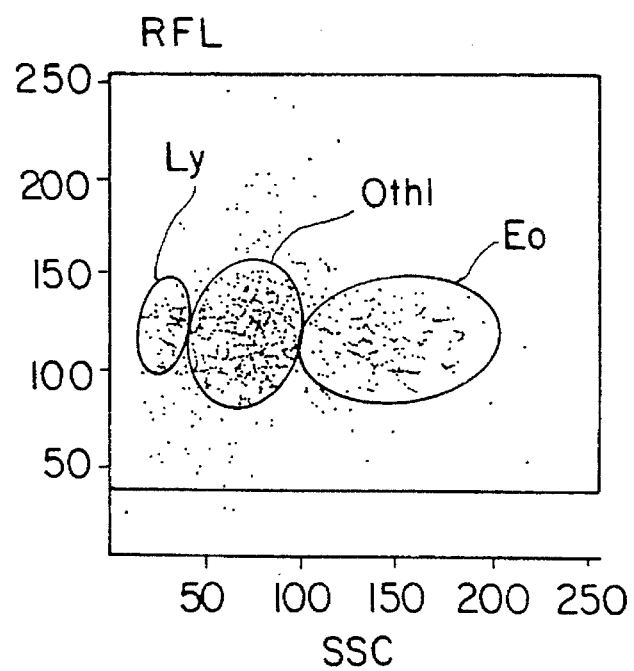
FIG. 13 is a scattergram showing the relationship between the intensity of the side scattered light (SSC) and the intensity of the red fluorescence light (RFL) when a blood is treated with $C_{18}H_{35}O—(CH_2CH_2O)_{20}—H$ as a nonionic surfactant.
Figure 14:
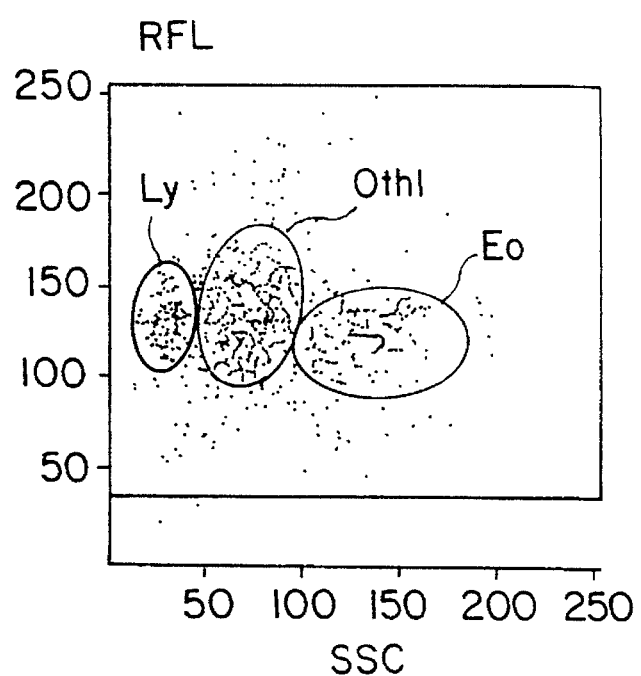
FIG. 14 is a scattergram showing the relationship between the intensity of the side scattered light (SSC) and the intensity of the red fluorescence light (RFL) when a blood sample is treated with $C_{18}H_{37}COO—(CH_2CH_2O)_{25}—H$ as a nonionic surfactant.
Figure 15:
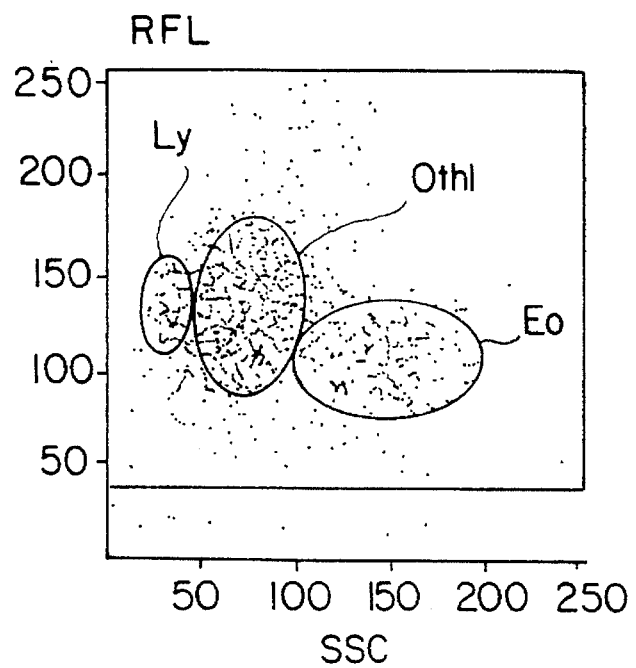
FIG. 15 is a scattergram showing the relationship between the intensity of the side scattered light (SSC) and the intensity of the red fluorescence light (RFL) when a blood sample is treated with a nonionic surfactant having the following formula.

FIG. 7 shows a scattergram wherein the side scattered light (SSC) and red fluorescence light (RFL) were measured without using an ionic surfactant. In this case, the lysing is strengthened by increasing the amount of LTAC, thereby excessively damaging the leukocytes. Unlike the results seen from FIG. 1 (LTAC 500 mg/l), it was observed that leukocytes are aggregated into one group, so that the leukocytes can not be classified.

In contrast, FIGS. 8 to 16 show that when various nonionic surfactants were contained in the surfactant, the damage of leukocytes was controlled and leukocytes can be classified and counted into lymphocytes (Ly), eosinophils (Eo), and other leukocytes (Oth1) with respect to every nonionic surfactant that was used. The molar number of addition of polyoxyethylene glycol and type of hydrophobic group did not affect the results.

Example 3: Function of Water Soluble Alcohol

A reagent having the following composition was prepared.

| | |
|---|---|
| HEPES-NaOH buffer (PH 7.0) | 10 mM |
| Ethidium bromide (EB) | 50 mg/l |
| LTAC | 250 mg/l |
| nonionic surfactant $C_{16}H_{33}O(CH_2CH_2O)_{30}$—H | 1,000 mg/l |
| Ethanol | 100–400 ml/l |

To the reagent (1.0 ml) having the above composition, venous blood (25 μl) which was treated with an anticoagulant was mixed. The red fluorescence light, forward scattered light, and side scattered light were measured by a flow cytometer.

FIGS. 17 to 19 show a scattergram wherein the side scattered light (SSC) and red fluorescence light (RFL) were measured when ethanol (100 ml/l) was contained in the treatment solution; a histogram thereof; and a scattergram obtained in the same manner as above by using the side scattered light (SSC) and red fluorescence light (RFL). As seen from these figures, leukocytes are classified and counted into four groups, i.e., lymphocytes (Ly), monocytes (Mo), eosinophils (Eo), and other leukocytes (Oth3).

FIGS. 20 to 22 show the case when ethanol (200 ml/l) was contained in the treatment solution. In this case, leukocytes are also classified and counted into four groups, i.e., lymphocytes (Ly), monocytes (Mo), eosinophils (Eo), and other leukocytes (Oth3).

FIGS. 23 to 25 show the case when ethanol (400 ml/l) was contained in the treatment solution. In this case, leukocytes are classified into three groups and counted, i.e., lymphocytes (Ly), eosinophils (Eo), and other leukocytes (Oth1).

Accordingly, it is observed that excessive use of ethanol prevents the obtaining of an optical difference of cells.

It is also observed that the lysis of erythrocytes is facilitated in accordance with an increase in the number of carbon atoms.

Example 4: Reagent Compositions Example

A reagent having the following composition were prepared.

| | |
|---|---|
| Lauryltrimethylammonium chloride (LTAC) (cationic surfactant) | 1 g |
| Brij35 (polyoxyethyleneglycol lauryl ether/molar number of addition: 23) (nonionic surfactant) | 1 g |
| Acridine Orange 10-dodecyl bromide (AO-10) (labeling substance: dye) | 0.100 g |
| Ethyl alcohol | 0.100 g |
| Citric acid monohydrate | 2.1 g |
| NaOH | adequate amount* |
| Purified water | 0.9 liter |

*NaOH is added in an amount so as to adjust the reagent to pH 4.

To the reagent (1.0 ml) having the above composition, venous blood (25 μl) which was treated with an anticoagulant was mixed. After 20 seconds at a room temperature, the red fluorescence light, green fluorescence light, forward scattered light, and side scattered light were measured by a flow cytometer.

FIGS. 26 to 28 show scattergrams obtained as results of normal subjects wherein the red fluorescence light (RFL) and green fluorescence light (GFL), side scattered light (SSC) and red fluorescence light (RFL), and forward scattered light (FSC) and red fluorescence light (RFL) are respectively measured. As seen from each figure, leukocytes are classified into three groups, i.e., lymphocytes (Ly), monocytes (Mo) and granulocytes (Gr). De indicates reduced erythrocyte membrane and blood platelet.

LTAC used in the present invention is a cationic surfactant and has a property of:

i) damaging to erythrocyte membranes to leak hemoglobins contained therein to convert the erythrocytes into ghosts, thereby making the erythrocytes optically transparent, and ii) damaging to leukocyte membranes so as to allow dye AO-10 to pass through the cell membranes.

The mechanism of the function of LTAC for damaging membranes of erythrocytes and leukocytes is not clear. However, it is considered that a part of lipid which constitutes cell membrane is lysed by the surface active action, resulting in forming trace pores in the cell membrane that allows passage of hemoglobin and dye.

Brij 35 is a nonionic surfactant. It controls the action of LTAC to inhibit the LTAC from severely damaging the cell membrane and cytoplasm to the degree that nuclei are made naked or the leukocytes are deformed. The agent also has a function for controlling the aggregation of erythrocytes that are converted into ghosts. Further, Brij 35 works for making AO-10, which has low water solubility, in an aqueous solution.

The dye AO-10 has a dodecyl group at the 10th position of orange. Acridine Orange is often used for staining DNA and RNA simultaneously. Since AO-10 does not usually pass through a cell membrane because of the steric hindrance of the long chain alkyl group, it merely stains cell membranes and the components contained in cells can not be stained. Therefore, the dye has been used only as a hydrophobic probe.

According to the present invention, as a cell membrane is damaged, AO-10 can invade into the cell and combine with components contained therein. When the dye is used for staining a blood sample as shown in the Examples, it combines with various components in the cell in a specific manner.

For example, in cytoplasm of lymphocytes and monocytes, AO-10 combines with RNA present in the cytoplasm by an ionic bond and stains this component orange, while a green fluorescence light is emitted from the nucleus and granules of the cells. It is inferred that in accordance with a conventionally known function of a hydrophobic probe, the long chain alkyl group of AO-10 is invaded through the nucleus membranes and granulocyte membrane to combine with the nucleus and granulocyte.

In the case of neutrophils, since the cytoplasm rarely has RNA, a green fluorescence light is emitted. From the nucleus and granules of neutrophils, a green light fluorescence light is emitted similar to the case of the nucleus and of the lymphocytes and monocytes.

The reason for these phenomena are considered that metachromatism occurs when AO-10 is combined with RNA, thereby staining RNA orange, while metachromasy does not occur in nuclei and granules because AO-10 combines with the surface of nuclei and granules, thereby emitting a green fluorescence light.

LTAC is combined with RNA by an ionic bond and the electric charges are neutralized, so that RNA is not lost from the cells. It is considered that AO-10 combines with such components which are thus not lost from cells.

In Examples of the present invention, blood samples taken from patients having a disease in blood were measured by using the reagent composition of the present invention.

FIGS. 29 to 31 show the results obtained from the samples sampled from patients having an acute myelocytic leukemia. Myeloblasts (My) were classified and counted.

FIGS. 32 to 34 show the results obtained from the samples in which Atypical lymphocytes (Aly) are erupted. Atypical lymphocytes (Aly) were classified and counted.

FIGS. 35 to 37 show the results obtained from the samples in which erythroblasts (Er) and immature granulocytes (Im) were erupted. As seen from these figures, Erythroblasts (Er) and immature granulocytes (Im) were classified and counted. Since Blast cells (Er) and (My), Atypical lymphocytes (Aly), Immature granulocytes (Im) include RNA richly therein, they can be detected by staining RNA. In addition, Reticulocytes (Ret) were partially detected from FIG. 37. In this example, erythrocytes are not completely lysed, but rather, only the membrane of the erythrocyte was damaged. Therefore, cell membranes of the cells which are converted into ghosts and RNA of the cell components are stained, thereby detecting reticulocytes.

Conventionally, dyes have not been used for the purpose of the present invention because dyes are hard to pass through cell membranes. However, according to the present invention, an effect of a dye which is different from the conventional use can be exhibited.

Example 5: Reagent Composition Example

A reagent having the following composition were prepared.

| | |
|---|---|
| Acridine Orange 10-dodecyl bromide (AO-10) (label substance) | 0.010 g |
| DiOC6 (3) (label substance) | 0.020 g |
| Lauryltrimethylammonium chloride (LTAC) (cationic surfactant) | 0.5 g |
| Polyoxyethyleneglycol cetyl ether (molar number of addition: about 40) (nonionic surfactant) | 1.0 g |
| Isopropyl alcohol | 0.050 liter |
| NaCl | 4.0 g |
| HEPES | 2.3 g |
| NaOH | Adequate Amount* |
| Purified water | 0.95 liter |

*NaOH is added in an amount so as to adjust the reagent to pH 7.0

To the reagent (1.0 ml) having the above composition, venous blood (25 μl) of normal subjects which was treated with an anticoagulant was mixed. After 20 seconds at a room temperature, the red fluorescence light, green fluorescence light, forward scattered light, side scattered light, and impedance signal were measured by a complex flow cytometer available for detecting not only optical differences but also impedance signals (IMP) based on the change of electric resistance.

In the present example, the damage to leukocytes minimized by using a smaller amount of cationic surfactants compared with the amount used in Example 4. In addition, as the reagent composition includes NaCl, impedance signals can be measured, and as the composition has a pH 5.0 or more, eosinophils can be also measured. Further, the dye DiOC6 (3) capable of staining granules well was added for facilitating separation of granules when measured by the red fluorescence light and green fluorescence light.

FIGS. 38 to 43 show scattergrams and a histogram when using the above reagent composition wherein the red fluorescence light (RFL) and green fluorescence light (GFL) (FIG. 38), side scattered light (SSC) and red fluorescence light (RFL) (FIG. 39), and side scattered light (SSC) and impedance signals (IMP) (FIG. 40) are respectively measured; side scattered light histogram (FIG. 41); scattergrams wherein side scattered light (SSC) and green fluorescence light (GFL) (FIG. 42), and side scattered light (SSC) and forward fluorescence light (FSC) (FIG. 43) are respectively measured. In these figures, Ne+Ba denotes a distribution of neutrophils and basophils.

In the present example, similar to Example 4, RNA can be stained. Therefore, Blast cells (Er) and (My), Atypical lymphocytes (Aly), Immature granulocytes (Im) can be classified and counted.

A flow cytometer disclosed in Japanese Patent Application Laid-Open H5-34251 (1993) (U.S. Ser. No. 07/902,979) was used for in this example to detect impedance signals.

Example 6: Reagent Composition Example

A reagent having the following composition were prepared.

| | |
|---|---|
| Lauryldimethylaminoacetic betaine (amphoteric surfactant) (Anon BL: produced by NIHON YUSHI Co.) | 2 g |
| Polyoxyethylene glycol nonylphenyl ether (molar number of addition: 20) (nonionic surfactant) | 1 g |
| Isopropyl alcohol | 0.100 liter |
| Citric acid monohydrate | 2.1 g |
| NaOH | Adequate Amount* |
| Propidium iodide | 0.1 g |
| Purified water | 0.9 liter |

*NaOH is added in an amount so as to adjust the reagent to pH 7.0

To the reagent (800 μl) having the above composition, venous blood (400 μl) which was treated with an anticoagulant was combined, and side scattered light and red fluorescence light were measured by a flow cytometer.

The present example aims to detect a trace amount of leukocytes in a reduced dilution which remain after the treatment by a filter for eliminating leukocytes. Generally, lysing agents available for obtaining volume differences are used at 100 to 200 times diluted concentration, so that it was not possible to use them for the preparation of reagent compositions having a high concentration such as those of the present example. In the case of using Triton X-100 conventionally used for a blood preparation, the ratio of blood:lysing agent is 1:7.5. However, more concentrated reagent compositions for measurement can be prepared in the present invention.

Further, according to the present invention, a scattergram similar to FIGS. 3 and 4 can be obtained and leukocytes can be classified into 3 groups. This is not possible if Triton X-100 is used.

Thus, reagent compositions having higher concentration at which measurements is not possible by conventional methods can be used by the method of the present invention.

Reference Example 1

For comparison, a reagent described in the specification of WO 84/003771 (a reagent comprising a cationic surfactant at a high concentration) was prepared as follows:

| | |
|---|---|
| Dodecyltrimethylammonium chloride (cationic surfactant) | 55 g/l |
| Tetradecyltrimethyltrimethylammonium | 9 g/l |

| | |
|---|---|
| chloride (Cationic surfactant) | |
| Potassium cyanide | 0.300 g/l |
| Polyoxyethylene glycol alkylphenol ether (Nonionic surfactant) | 12 ml/l |

To the reagent (1.0 ml) having the above composition, venous blood (25 μl) which was treated with an anticoagulant was combined. After incubating for 20 seconds, the side scattered light and red fluorescence light were measured by a flow cytometer. The results are shown in FIGS. 44 and 45.

As seen from the figures, the leukocytes are aggregated into one population, so that they can not be classified by the side scattered light and red fluorescence light based on an optical difference.

Reference Example 2

A reagent which comprises a nonionic surfactant was prepared as follows and used to perform a DNA staining.

| | |
|---|---|
| Nonidet P-40 (Nonionic surfactant) | 1 ml/l |
| Sodium Citrate | 10 g/l |

To the reagent (1.0 ml) having the above composition, propidium iodide (50 μg/ml) was added, then venous blood (25 μl) which was treated with an anticoagulant was combined. After incubating for 20 seconds, the side scattered light and red fluorescence light were measured by a flow cytometer. The results are shown in FIGS. 46 and 47.

As seen from the figures, the eosinophils can be identified by the side scattered light and red fluorescence light based on the optical difference because they were not made into naked nuclei. However, leukocytes other than eosinophils can not be classified into subclasses.

According to the present invention, 1. the property of a labeling substance for passing through cell membrane can be enhanced by treating a biological sample with an aqueous solution comprising a cationic and/or amphoteric surfactant a labeling substance without a treatment such as fixing. As a result, cells can be labeled with various labeling substances almost instantly. In addition, while eliminating the influence of erythrocytes, optical differences, which were not previously measurable, can be obtained by the scattered light and the like by using the surfactants.
2. Since the problem of transmittance of a labeling substance to a cell membrane is solved, labeling substances which have been considered not to be used for cell classification can be made available for such classification use.
3. As the results, a property of labeling substances different from the conventional property can be found (for example, portion available to dye, etc.).
4. Precise classification of cells which has not been achieved in prior art can be performed by using the composition containing nonionic surfactant and alcohol.
5. The present invention can be also used for examining the cell staining properties of labeling substances.

What I claim is:

1. A method for classifying and counting leukocytes by an optical means which comprises;

(i) treating a blood sample containing leukocytes with an aqueous solution having a pH ranging from 5.0 to 11.0 and comprising an ionic surfactant and a fluorescent dye, to give an optical difference between eosinophils and other leukocytes, wherein the ionic surfactant is used at a concentration effective to not damage the whole of the cell membrane of leukocytes in the blood sample but effective to damage a part of the cell membrane so as to allow the fluorescent dye to enter the leukocytes and stain intracellular material, and wherein said ionic surfactant is at least one selected from the group consisting of:

a) a quaternary ammonium salt of the following formula:

$$R_2 - \overset{\overset{R_1}{|}}{\underset{\underset{R_3}{|}}{N^+}} - R_4 \quad X^-$$

wherein $R_1$, $R_2$ and $R_3$ are independently a hydrogen atom, a $C_1$–$C_8$ alkyl group or a $C_6$–$C_8$ aralkyl group; $R_4$ is a $C_8$–$C_{18}$ alkyl group, a $C_8$–$C_{18}$ alkenyl group or a $C_8$–$C_{18}$ aralkyl group; and $X^-$ is an anion, b) a pyridinium salt surfactant of the following formula:

$$\langle\!\langle\bigcirc\rangle\!\rangle N^+ - R_5 \quad X^-$$

wherein R5 is a C8–C18 alkyl group; and $X^-$ is an anion, and c) an amphoteric surfactant of the following formula:

$$R_7 - \overset{\overset{R_6}{|}}{\underset{\underset{R_8}{|}}{N^+}} - (CH_2)_n COO^-$$

wherein $R_6$ and $R_7$ are independently a hydrogen atom or a $C_1$–$C_8$ alkyl group; $R_8$ is a $C_8$–$C_{18}$ alkyl group; and n is 1 or 2;

and (II) classifying and counting the leukocytes by measuring an optical difference between eosinophils and other types of leukocytes in the blood sample based on at least two kinds of light selected from the group consisting of forward scattered light, side scattered light, red fluorescence light and green fluorescence light.

2. A method according to claim 1, wherein one of said at least two kinds of light is side scattered light.

3. A method according to claim 1, in which a concentration of the ionic surfactant is 30 to 5000 mg/l.

4. A method according to Claim 1, in which the aqueous solution further contains at least one nonionic surfactant of the following formula:

$$R_9 R_{10}(CH_2CH_2O)_n H$$

wherein $R_9$ is a $C_8$–$C_{22}$ alkyl group or a $C_8$–$C_{22}$ alkenyl group;

$R_{10}$ is $$-O-, \quad -COO- \quad \text{or} \quad -\!\!\langle\bigcirc\rangle\!\!-O-;$$

and n is an integer not less than 10;

to give an optical difference among at least three groups of leukocytes comprising eosinophils, lymphocytes and other types of leukocytes.

5. A method according to claim 4, in which a concentration of the nonionic surfactant is 100 to 10000 mg/l.

6. A method according to claim 4, in which the aqueous solution further contains at least one water-soluble alcohol with not less than 2 carbons to give an optical difference among at least four groups of leukocytes comprising eosinophils, lymphocytes, monocytes and other types of leukocytes.

7. A method according to claim 6, in which the water-soluble alcohol is ethyl alcohol and is used at concentration of 50 to 400 ml/L.

8. A method according to any one of claims 1–7, in which the aqueous solution contains a basic fluorescent dye as the fluorescent dye, and the optical difference is measured by at least one of red fluorescence light and green fluorescence light.

9. A method according to claim 8, in which the fluorescent dye is a fluorescent dye that can combine at least with cell nuclei, and is at least one dye selected from the group consisting of propidium iodide and ethidium bromide.

10. A method according to claim 8, in which the fluorescent dye is a fluorescent dye that can combine at least with cellular RNA, and is at least one dye selected from the group consisting of pyronin Y, Acridine Orange, Thiazole Orange, Acridine Orange 10 dodecyl bromide and Auramine O.

11. A method according to claim 10, in which the aqueous solution contains Acridine Orange 10 dodecyl bromide as the fluorescent dye, and the optical difference is measured based on at least the red fluorescence light.

12. A method according to claim 11, in which the fluorescent dye further contains 3,3'-dihexyloxacarbocyanine, and the optical difference is measured by at least the green fluorescence light.

13. A method according to claim 12, in which the aqueous solution further contains a sufficient amount of a salt for measuring impedance signals as electric conductivity, and further in which a difference in impedance signals is measured for counting and classifying leukocytes.

14. A method of classifying and counting leukocytes by an optical means comprising;
(i) treating a blood sample containing leukocytes with an aqueous solution having a pH ranging from 3.0 to 5.0 and containing an ionic surfactant, a nonionic surfactant, a water-soluble alcohol having at least two carbon atoms, and Acridine Orange 10 dodecyl bromide, to give an optical difference among groups of leukocytes comprising lymphocytes, monocytes, granulocytes and other types of leukocytes;

wherein the ionic surfactant is used at a concentration effective to not damage the whole of the cell membrane of leukocytes in the blood sample but effective to damage a part of the cell membrane so as to allow the Acridine Orange 10 dodecyl bromide to enter the leukocytes and stain intracellular material and wherein the ionic surfactant is at least one quaternary ammonium salt of the following formula:

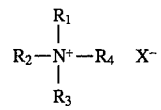

wherein $R_1$, $R_2$ and $R_3$ are independently a hydrogen atom, a $C_1$–$C_8$ alkyl group or a $C_6$–$C_8$ aralkyl group; $R_4$ is a $C_8$–$C_{18}$ alkyl group, a $C_8$–$C_{18}$ alkenyl group or a $C_8$–$C_{18}$ aralkyl group; and $X^-$ is an anion, and wherein the nonionic surfactant is of the following formula:

wherein $R_9$ is a $C_8$–$C_{22}$ alkyl group or a $C_8$–$C_{22}$ alkenyl group;

$R_{10}$ is

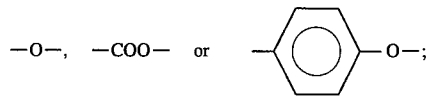

n is an integer not less than 10; and (ii) classifying and counting the leukocytes by measuring an optical difference in at least two kinds of light selected from the group consisting of forward scattered light, side scattered light, red fluorescence light and green fluorescence light among groups of leukocytes comprising lymphocytes, monocytes, granulocytes and other types of leukocytes.

\* \* \* \* \*